(12) United States Patent
Imai

(10) Patent No.: US 9,060,677 B2
(45) Date of Patent: Jun. 23, 2015

(54) ENDOSCOPE

(71) Applicant: OLYMPUS MEDICAL SYSTEMS CORP., Tokyo (JP)

(72) Inventor: Shunichi Imai, Okaya (JP)

(73) Assignee: OLYMPUS MEDICAL SYSTEMS CORP., Tokyo (JP)

( * ) Notice: Subject to any disclaimer, the term of this patent is extended or adjusted under 35 U.S.C. 154(b) by 0 days.

(21) Appl. No.: 13/649,660

(22) Filed: Oct. 11, 2012

(65) Prior Publication Data

US 2013/0131453 A1     May 23, 2013

Related U.S. Application Data

(63) Continuation of application No. PCT/JP2012/060062, filed on Apr. 12, 2012.

(30) Foreign Application Priority Data

Apr. 13, 2011  (JP) .................................. 2011-089474

(51) Int. Cl.
| | |
|---|---|
| *A61B 1/12* | (2006.01) |
| *A61B 1/00* | (2006.01) |
| *G02B 23/24* | (2006.01) |
| *A61B 1/018* | (2006.01) |
| *A61B 1/06* | (2006.01) |

(Continued)

(52) U.S. Cl.
CPC ............. *A61B 1/00091* (2013.01); *A61B 1/126* (2013.01); *G02B 23/2476* (2013.01); *A61B 1/00094* (2013.01); *A61B 1/00096* (2013.01); *A61B 1/00114* (2013.01); *A61B 1/018* (2013.01); *A61B 1/0684* (2013.01); *A61B 1/07* (2013.01); *A61B 1/12* (2013.01)

(58) Field of Classification Search
CPC ........................ A61B 1/00091; A61B 1/00137
USPC ............. 600/155–158, 104, 127, 129; 348/45
See application file for complete search history.

(56) References Cited

U.S. PATENT DOCUMENTS 4,281,646 A * 8/1981 Kinoshita ..................... 600/157
4,991,957 A * 2/1991 Sakamoto et al. .......... 356/241.4
(Continued)

FOREIGN PATENT DOCUMENTS

| EP | 1692995 A1 | 8/2006 |
|---|---|---|
| EP | 2594187 A1 | 5/2013 |

(Continued)

OTHER PUBLICATIONS

Machine Translation of Nakakawanishi Japanese Patent H08-215137, Aug. 27, 1996; translation performed May 7, 2014.*

(Continued)

*Primary Examiner* — Anhtuan T Nguyen
*Assistant Examiner* — Timothy J Neal
(74) *Attorney, Agent, or Firm* — Oliff PLC

(57) ABSTRACT

An endoscope includes an insertion portion which includes a distal end hard portion having a hole portion passed through a distal end surface, and a nozzle including an opening. The nozzle includes a cover member including an annular portion, a cylindrical coupling portion coupled with the distal end hard portion and a cylindrical core member which has one end having the annular portion arranged thereon and the other end having the coupling portion arranged thereon and which includes a flow path communicating with the opening.

14 Claims, 25 Drawing Sheets

(51) Int. Cl.
*A61B 1/07* (2006.01)
*A61B 1/04* (2006.01)

(56) References Cited

U.S. PATENT DOCUMENTS

| | | | |
|---|---|---|---|
| 5,725,474 A * | 3/1998 | Yasui et al. | 600/127 |
| 5,871,440 A * | 2/1999 | Okada | 600/129 |
| 2007/0038027 A1 | 2/2007 | Miyagi et al. | |
| 2011/0201884 A1 | 8/2011 | Kishioka | |

FOREIGN PATENT DOCUMENTS

| | | | | |
|---|---|---|---|---|
| JP | A-04-371131 | 12/1992 | | |
| JP | 08215137 A * | 8/1996 | | A61B 1/00 |
| JP | A-9-201328 | 8/1997 | | |
| JP | H11-197095 A | 7/1999 | | |
| JP | A-11-318809 | 11/1999 | | |
| JP | A-2000-083891 | 3/2000 | | |
| JP | 2004-41430 A | 2/2004 | | |
| JP | A-2010-035587 | 2/2010 | | |
| JP | 2010-119569 A | 6/2010 | | |
| WO | 2010/101149 A1 | 9/2010 | | |

OTHER PUBLICATIONS

Japanese Office Action issued in Japanese Application No. 2012-547386 dated Nov. 27, 2012 (w/translation).
Oct. 24, 2013 International Preliminary Report on Patentability issued in Japanese Patent Application No. PCT/JP2012/060062 (with English Translation).
International Search Report issued in International Application No. PCT/JP2012/060062 dated May 22, 2012 (with translation).
Jan. 5, 2015 Office Action issued in Chinese Application No. 201280011687.8.
Feb. 12, 2015 Supplementary Partial European Search Report issued in European Application No. EP 12 77 1000.2.

* cited by examiner

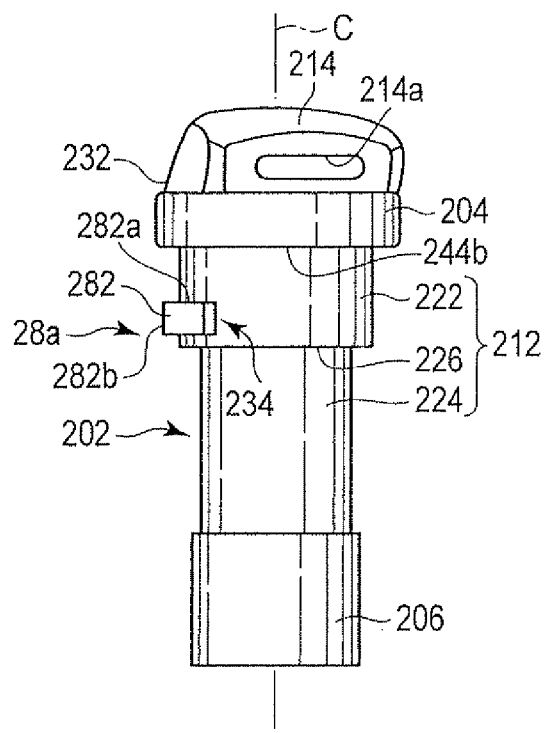
F I G. 20
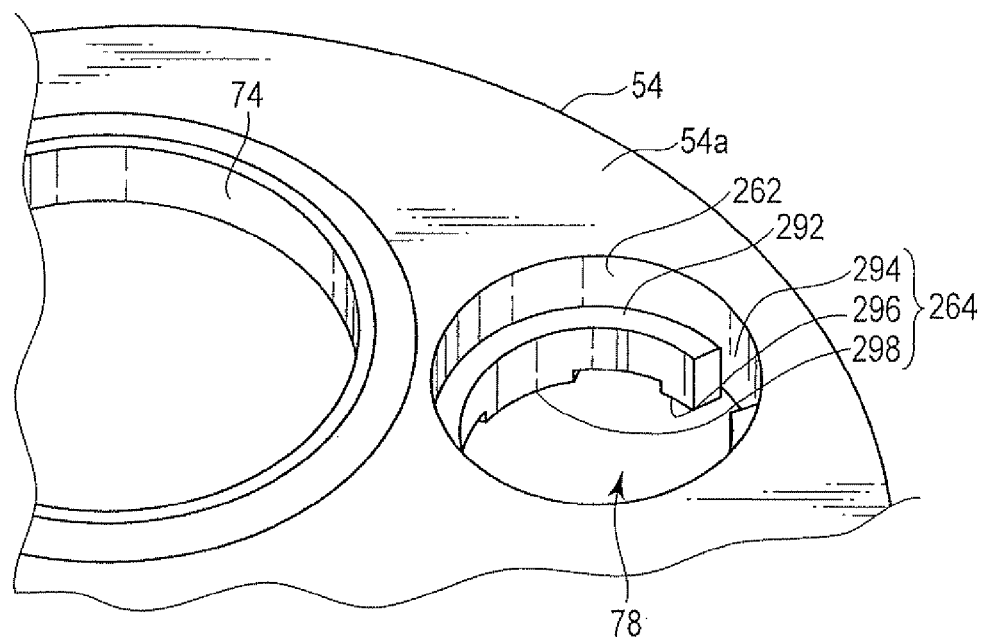
F I G. 21A

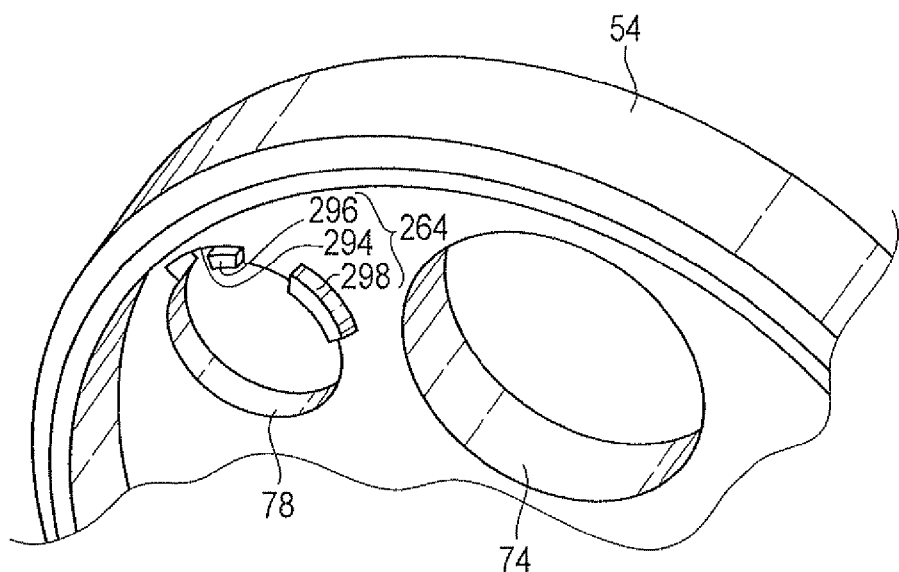
F I G. 21B
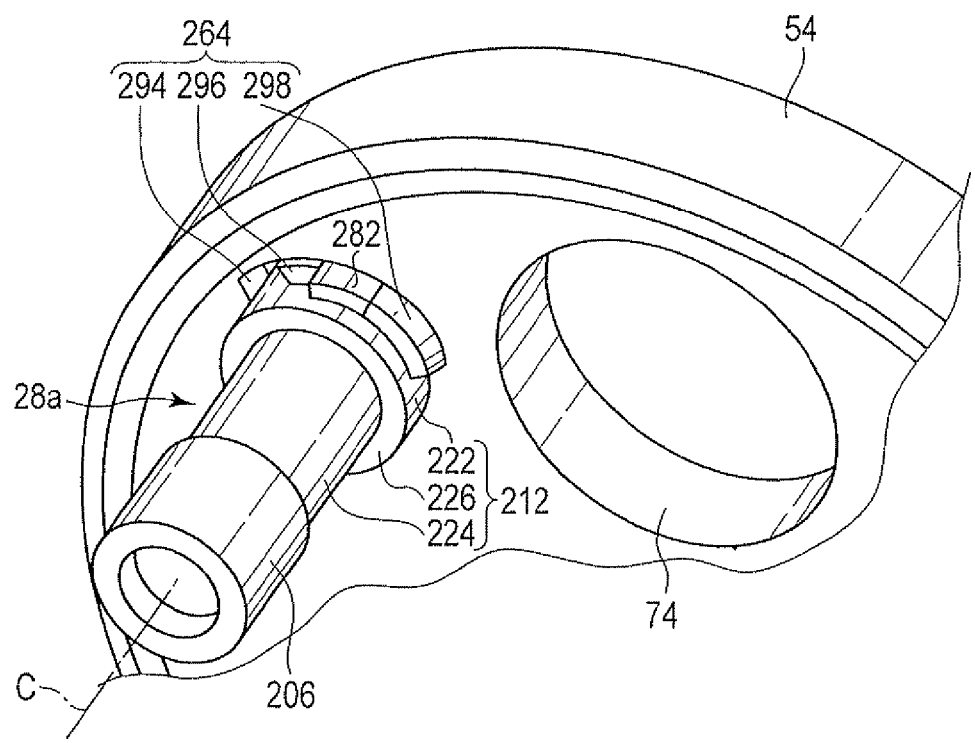
F I G. 22

ENDOSCOPE

CROSS-REFERENCE TO RELATED APPLICATIONS

This is a Continuation Application of PCT Application No. PCT/JP2012/060062, filed Apr. 12, 2012, which was published under PCT Article 21(2) in Japanese.

This application is based upon and claims the benefit of priority from the prior Japanese Patent Application No. 2011-089474, filed Apr. 13, 2011, the entire contents of which are incorporated herein by reference.

BACKGROUND OF THE INVENTION

1. Field of the Invention

The present invention relates to an endoscope including a nozzle at a distal end portion of an insertion portion.

2. Description of the Related Art

For example, Jpn. Pat. Appln. KOKAI Publication No. 2000-83891 discloses an air supply/water supply nozzle which is attachable to/detachable from a distal end portion of an insertion portion. The nozzle is fixed to the distal end portion of the insertion portion by heating a resin material through the nozzle and fusing the resin material with respect to the distal end portion of the insertion portion and then cooling and solidifying the fused resin material.

BRIEF SUMMARY OF THE INVENTION

An endoscope according to the invention includes: a distal end hard portion provided at a distal end portion of an insertion portion; and a nozzle which is arranged to pass through the distal end hard portion and configured to eject a fluid, wherein the distal end hard portion includes: a cylindrical distal end portion main body which includes a first hole portion in which the nozzle is arranged; and a distal end cover which includes a second hole portion coaxially provided with the first hole portion and a first engagement portion provided at an edge portion of the second hole portion, and which is configured to cover an outer periphery of the distal end portion main body, and the nozzle includes: a cylindrical core member which includes: one end, the other end, a flow path through which the fluid is allowed to flow toward the one end from the other end, and a nozzle opening which is arranged at the one end and arranged at a position protruding from a distal end surface of the distal end cover; a second engagement portion which is provided on an outer side of the core member, elastically deformable, has self-restoration properties to hold its shape, is engaged with the first engagement portion of the distal end cover, and is configured to secure air-tightness and water-tightness in the insertion portion; and a cylindrical coupling portion which is arranged at the other end of the core member and coupled with the first hole portion of the distal end portion main body.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 20 is a schematic perspective view showing a nozzle attached to a distal end hard portion of an insertion portion of an endoscope according to a second modification of the second embodiment;

FIG. 21A is a schematic perspective view showing an air supply/water supply hole portion on a front surface side of a distal end cover at the distal end hard portion of the insertion portion of the endoscope according to the second modification of the second embodiment;

FIG. 21B is a schematic perspective view showing an air supply/water supply hole portion on a back surface side of the distal end cover at the distal end hard portion of the insertion portion of the endoscope according to the second modification of the second embodiment; and FIG. 22 is a schematic perspective view showing a state that the nozzle is attached to the distal end hard portion of the insertion portion of the endoscope according to the second modification of the second embodiment.

DETAILED DESCRIPTION OF THE INVENTION

Mode for embodying the present invention will now be described hereinafter with reference to the drawings.

First Embodiment

A first embodiment will now be described with reference to FIG. 1A to FIG. 5B.

As shown in FIG. 1, an endoscope 10 includes an insertion portion 12, an operation portion 14, and a universal cable 16. If the endoscope 10 according to this embodiment is used for medical purposes, the insertion portion 12 is inserted into a patient's body cavity, and the operation portion 14 is gripped by an operator and used for appropriately moving the insertion portion 12.

Figure 2:
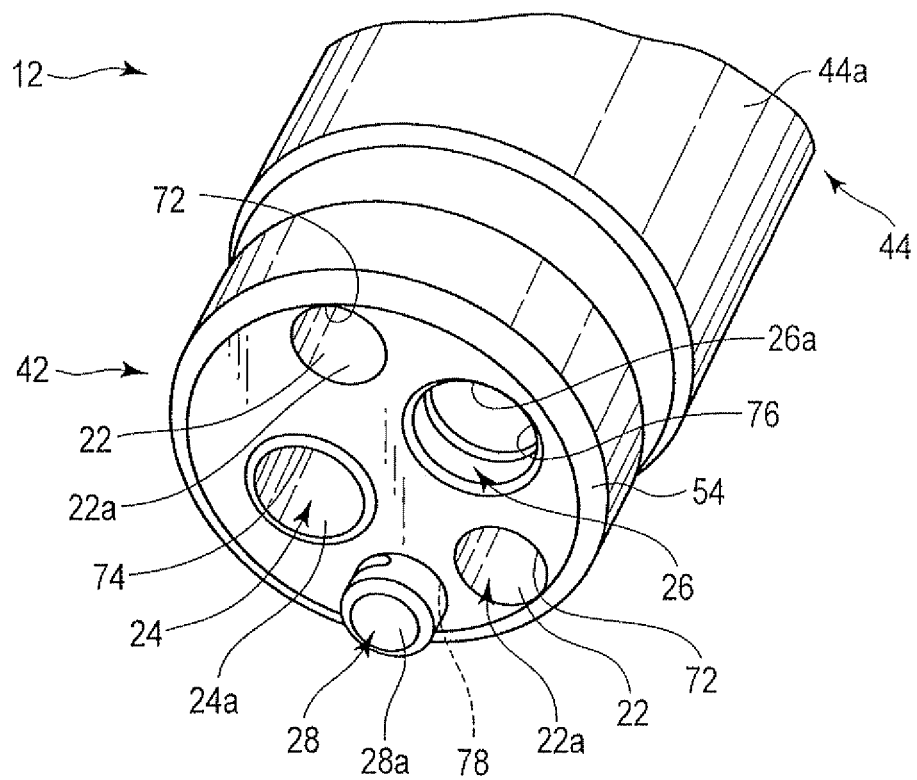
FIG. 2 is a schematic perspective view showing a distal end hard portion of an insertion portion of the endoscope according to the first embodiment.
Figure 3A:
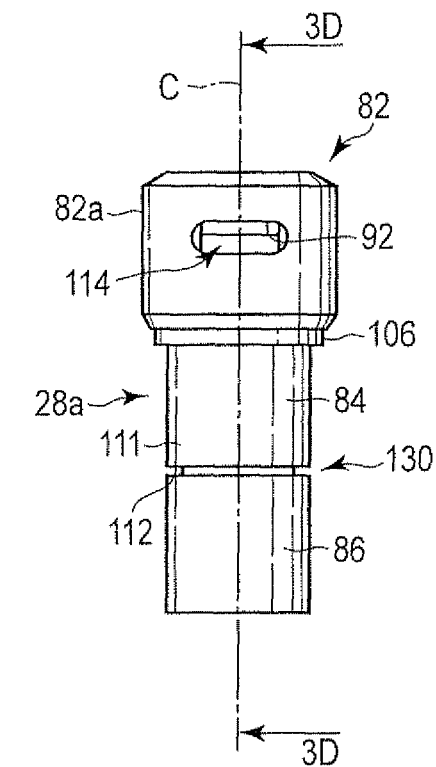
FIG. 3A is a front view showing a nozzle attached to the distal end hard portion of the insertion portion of the endoscope according to the first embodiment.
Figure 3B:
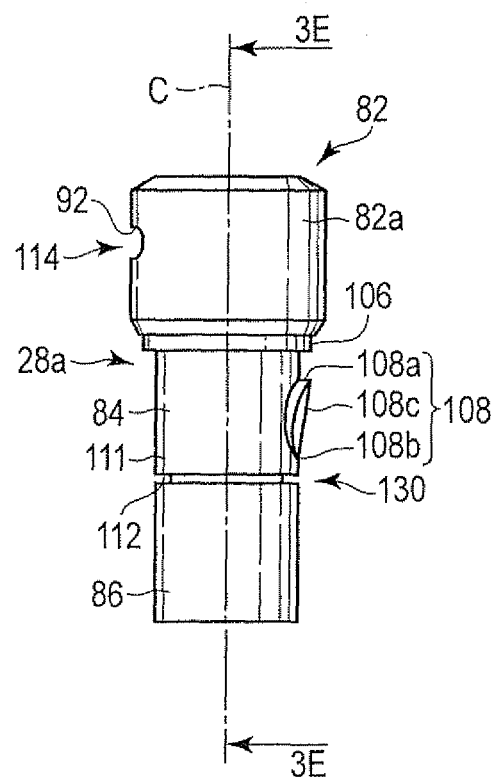
FIG. 3B is a right side view showing the nozzle attached to the distal end hard portion of the insertion portion of the endoscope according to the first embodiment.
Figure 3C:
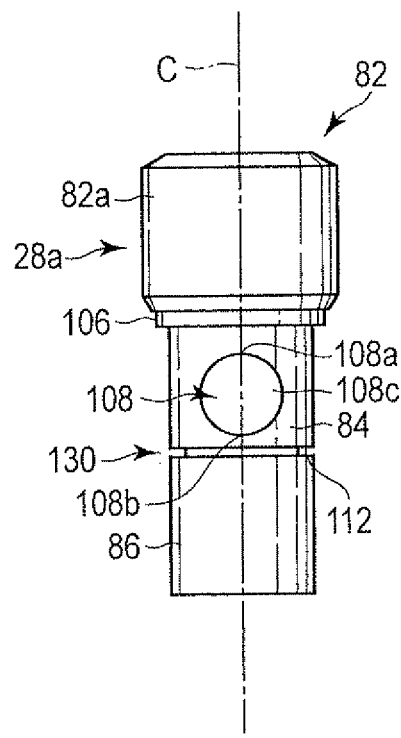
FIG. 3C is a back view showing the nozzle attached to the distal end hard portion of the insertion portion of the endoscope according to the first embodiment.
Figure 3D:
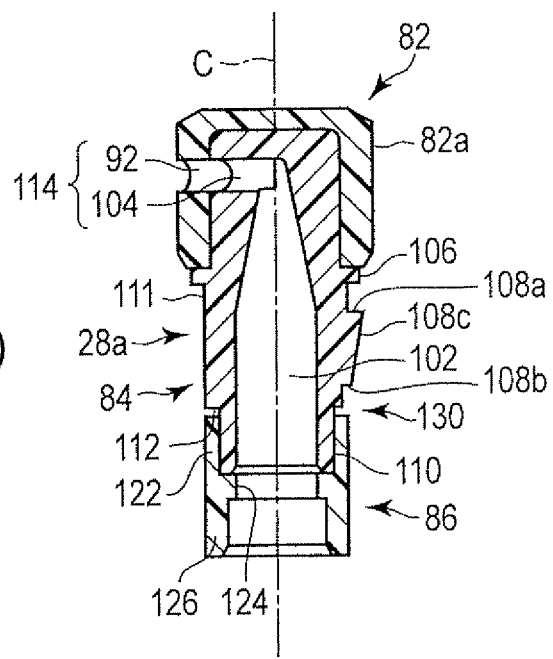
FIG. 3D is a cross-sectional view which shows the nozzle attached to the distal end hard portion of the insertion portion of the endoscope according to the first embodiment, and is taken along a line 3D-3D in FIG. 3A.
Figure 3E:
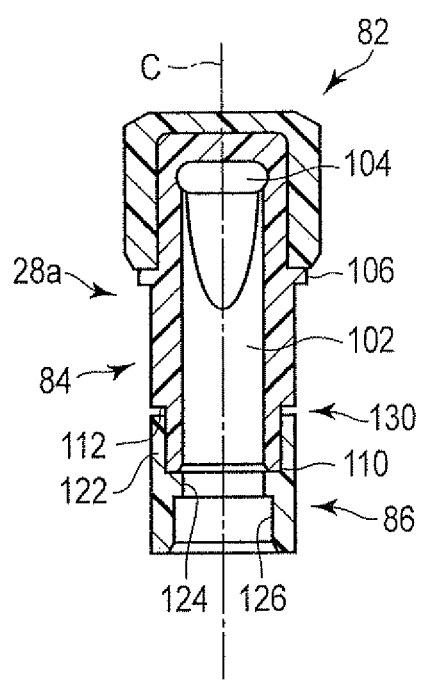
FIG. 3E is a cross-sectional view which shows the nozzle attached to the distal end hard portion of the insertion portion of the endoscope according to the first embodiment, and is taken along a line 3E-3E in FIG. 3B.

The insertion portion 12 is formed into a tubular shape and, as shown in FIG. 2, in the insertion portion 12 are inserted an illumination optical system 22 which includes a pair of illumination windows (illumination lenses) 22a at a distal end of the insertion portion 12 and illuminates a subject, an observation optical system 24 which includes an observation window (an objective lens) 24a at the distal end of the insertion portion 12 and is used for observing a subject, a channel 26 which includes a channel opening 26a at the distal end of the insertion portion 12 and a treatment tool or the like inserted therein and is also used as a suction path, and an air supply/water supply path (a fluid path) 28 which includes a nozzle 28a at the distal end of the insertion portion 12 and through which a cleaning liquid (e.g., a normal saline solution) or compressed air is supplied to the observation window 24a. The illumination windows 22a, the observation window 24a, the channel opening 26a, and the nozzle 28a are arranged at a later-described distal end hard portion 42 of the insertion portion 12, respectively, and the illumination optical system 22 is extended from the illumination windows 22a toward the operation portion 14, the observation optical system 24 is extended from the observation window 24a toward the same, the channel 26 is extended from the channel opening 26a toward the same, and the air supply/water supply path 28 is extended from the nozzle 28a toward the same. In the distal end hard portion 42, the observation window 24a and the channel opening 26a are arranged between the pair of illumination windows 22a, and the nozzle 28a is arranged to be adjacent to the observation window 24a. It is preferable for distances between the observation window 24a and the pair of illumination windows 22a to be the same.

In the insertion portion 12, the well-known illumination optical system 22 and observation optical system 24 which are not shown in detail are used. For example, a light guide fiber or an LED is arranged on a rear end side of each illumination window 22a, and the illumination optical system 22 emits illumination light through each illumination window 22a and illuminates a subject. For example, an imaging unit 24b (see FIG. 5A) is arranged on a rear end side of the observation window 24a, and the observation optical system 24 acquires a subject image illuminated with the illumination light through the observation window 24a.

Figure 1A:
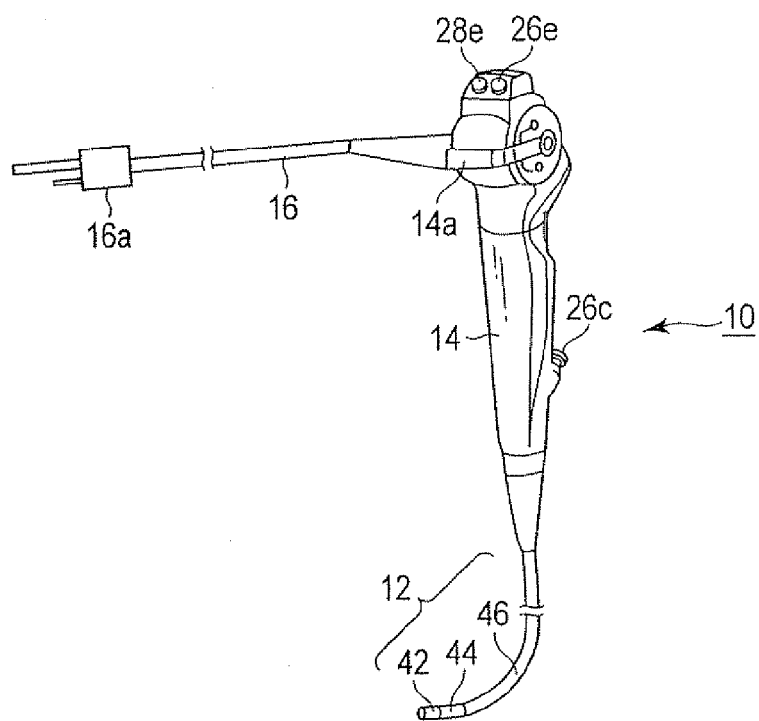
FIG. 1A is a schematic view showing an outside appearance of an endoscope according to a first embodiment.
Figure 1B:
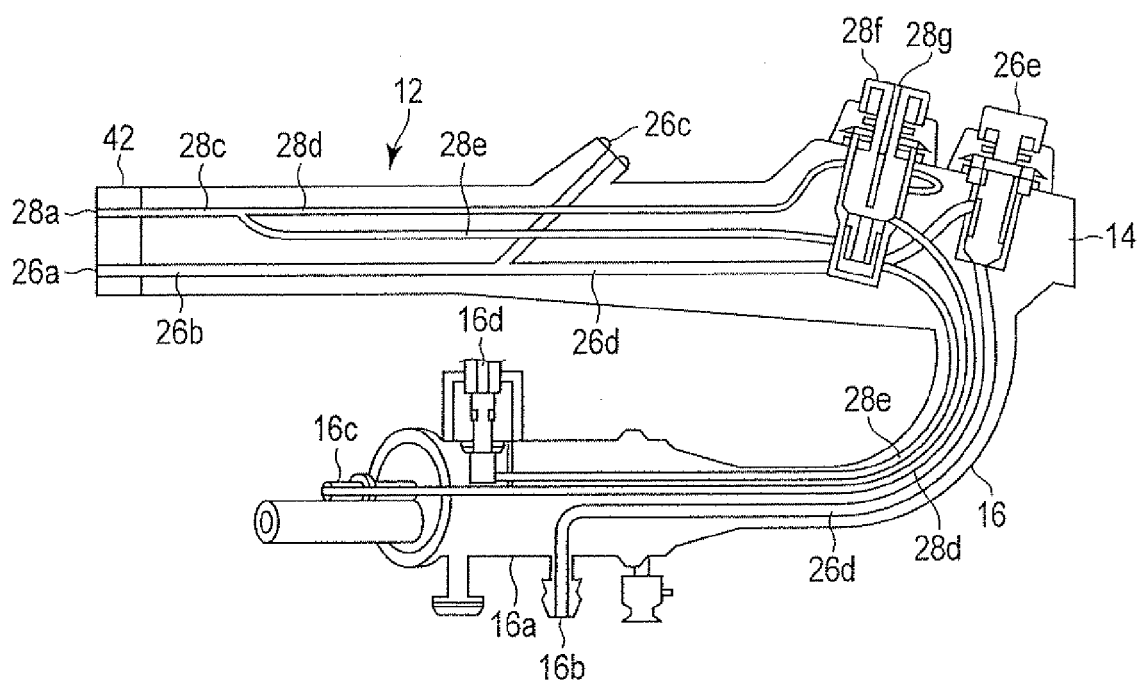
FIG. 1B is a schematic view showing conduit lines arranged in the endoscope.

As shown in FIG. 1B, a flexible tube 26b is arranged on a rear end side of the channel opening 26a, and the channel 26 allows, e.g., a forceps to protrude toward a subject from the distal end of the insertion portion 12 through a forceps plug 26c arranged in the operation portion 14 and performs various kinds of treatments with respect to the subject. Further, a suction tube 26d is connected to the flexible tube 26b. Since a tube from a forceps opening in which the forceps plug 26c is arranged and the suction tube 26d join together in, e.g., the operation portion 14, and the channel opening 26a can be used as a forceps opening and also used as a suction opening. Furthermore, when a suction button 26e arranged in the operation portion 14 is pressed, a conduit is opened, and suction is carried out by using a suction unit (not shown) connected to a mouth ring 16b in a connector 16a of the universal cable 16.

An air supply/water supply pipe 28b made of a hard material such as a stainless steel material is arranged on a rear end side of the nozzle 28a of the air supply/water supply path 28. The air supply/water supply pipe 28b is fixed to or integrally formed with a later-described distal end portion main body 52. As will be described later, when a coupling portion 86 of the nozzle 28a is coupled with the air supply/water supply pipe 28b, an outer peripheral surface of the air supply/water supply pipe 28b can be in close contact with an inner peripheral surface of a proximal end-side cylindrical portion 126 of the coupling portion 86.

An air supply/water supply tube (a fluid tube) 28c is fixed to a rear end side of the air supply/water supply pipe 28b. Like a general water hose, it is preferable for the air supply/water supply tube 28c to be made of a resin material which has flexibility and hardly squashes.

An air supply tube 28d and a water supply tube 28e are bifurcated on a rear end side of the air supply/water supply tube 28c. The air supply tube 28d and the water supply tube 28e are extended from the insertion portion 12 to the connector 16a of the universal cable 16 through the operation portion 14. Moreover, the air supply tube 28d is connected to a pump (not shown) arranged to a non-illustrated light source connected to the illumination optical system 22 through a mouth ring 16c of the connector 16a, and the water supply tube 28e is connected to a water supply bottle (not shown) through a mouth ring 16d of the connector 16a.

Air is constantly supplied from the pump through the air supply tube 28d, and this air is usually discharged from a hole 28g of an air supply/water supply button 28f arranged in the operation portion 14. When the hole 28g of the air supply/water supply button 28f is closed with a finger of an operator of the endoscope 10, the air is discharged from the air supply/water supply nozzle 28a through the air supply tube 28d, the air supply/water supply tube 28c, and the air supply/water supply pipe 28b. On the other hand, when the air supply/water supply button 28f is pressed, since the air supply tube 28d is blocked in the operation portion 14, the air supplied to the air supply tube 28d applies a pressure to the water supply bottle, and water (the normal saline solution) in the water supply bottle is discharged from the air supply/water supply nozzle 28a through the water supply tube 28e, the air supply/water supply tube 28c, and the air supply/water supply pipe 28b.

It is to be noted that the air supply/water supply tube 28c, the air supply tube 28d, and the water supply tube 28e are passively bent and arranged between the air supply/water supply button 28f and the distal end of the insertion portion 12 in a loosened state. Therefore, for example, when a later-described bending portion 44 is bent, excessive force can be prevented from being applied to the air supply/water supply tube 28c, the air supply tube 28d, and the water supply tube 28e, and a distal end position of the air supply/water supply tube 28c with respect to the later-described distal end hard portion 42 can be maintained.

As shown in FIG. 1A, the insertion portion 12 includes the distal end hard portion 42, the bending portion 44, and a tubular body 46 from its distal end portion (a far side with respect to the operation portion 14) toward its proximal end portion (the operation portion 14 side) in the mentioned order. As the tubular body 46, a so-called corrugated tube shown in FIG. 1A may be used, or a hard pipe (not shown) that is hardly deformed even if force is applied thereto may be used. In case of using the hard pipe, a metal material such as a stainless steel material or a plastic material such as a reinforced resin is adopted.

The bending portion 44 includes a bending tube in which, for example, well-known bending pieces are aligned along an axial direction of the insertion portion 12, and the bending pieces adjacent to each other can relatively revolve with respect to each other. Further, a distal end of a wire is fixed to the bending piece on the outermost distal end side, and this wire is sequentially inserted to the adjacent bending piece on the proximal end side. A proximal end of the wire is extended to, e.g., the operation portion 14 through the tubular body 46. When an operator operates a knob 14a of the operation portion 14 and moves the wire along its axial direction, the bending portion 44 can be appropriately bent. It is to be noted that an envelope tube 44a (see FIG. 2) covers an outer layer of the bending portion 44.

The distal end hard portion 42 includes a distal end portion main body 52 and a distal end cover 54 that is disposed to a distal end side of the distal end portion main body 52 and covers an outer peripheral surface of the distal end portion main body 52, and respective distal ends of the illumination optical system 22, the observation optical system 24, the channel 26, and the air supply/water supply path 28 are fixed to the distal end portion main body 52 and the distal end cover 54, respectively.

The distal end portion main body 52 is formed into a substantially cylindrical shape by using, e.g., a metal material such as a stainless steel material or a hard resin material. The distal end cover 54 protects the distal end side of the distal end portion main body 52, and it is formed into a substantially cylindrical shape by using a resin material having heat-resisting properties, insulation properties, acid-resisting properties, base-resisting properties, and others such as polysulphone.

In the distal end portion may body 52 are formed an illumination optical system hole portion (not shown) in which the illumination optical system 22 is arranged, an observation optical system hole portion 64 in which the observation optical system 24 is arranged, a channel hole portion (not shown), and an air supply/water supply hole portion (a first hole portion) 68 in which the air supply/water supply nozzle 28a is arranged.

Furthermore, it is preferable for a diameter of the air supply/water supply hole portion 68 to be formed constant and slightly smaller than a diameter of each of a later-described core member 84 and coupling portion 86 of the nozzle 28a. Since the core member 84 and the coupling portion 86 are made of an elastic material more flexible than that of the distal end portion main body 52, an outer peripheral surface of each of the core member 84 and the coupling portion 86 can be appressed against an inner peripheral surface of the air supply/water supply hole portion 68.

It is also preferable that the diameter of the air supply/water supply hole portion 68 is not constant and the air supply/water supply hole portion 68 is formed into a tapered shape that is larger on a distal end surface 52a side of the distal end portion main body 52 and gradually becomes smaller as getting closer to the opposite side. In this case, it is preferable for a taper angle of the inner peripheral surface of the air supply/water supply hole portion 68 to be gentle (for example, a tilt is as very small as approximately several degrees). Then, in a state that the later-described coupling portion 86 is elastically deformed and arranged in the air supply/water supply hole portion 68 of the distal end portion main body 52, the coupling portion 86 can be assuredly held.

An outside diameter of a later-described flange 106 of the core member 84 is larger than a diameter of the air supply/water supply hole portion 68, and the flange 106 of the core member abuts on the distal end surface 52a of the distal end portion main body 52.

A through hole 68a is formed in the air supply/water supply hole portion 68 toward the outer side of a side surface of the distal end portion main body 52. The through hole 68a has a central axis C1 in, e.g., a direction orthogonal to the axial direction of the insertion portion 12 which is parallel to a later-described central axis C. It is to be noted that a shape of the through hole 68a is described as a circular shape, but various kinds of shapes such as an elliptic shape or a polygonal shame may be adopted. A boss portion 108 of the later-described core member 84 of the nozzle 28a is formed into the same shape as that of the through hole 68a.

As shown in FIG. 2, in the distal end cover 54 are formed illumination optical system hole portions 72 in which the respective illumination windows 22a of the illumination optical system are arranged, an observation optical system hole portion 74 in which the observation window 24a of the observation optical system 24 is arranged, a channel hole portion 76 that forms the channel opening 26a, and an air supply/water supply hole portion (a second hole portion) 78 in which the nozzle 28a is arranged. The distal end surface 54a and a side surface 54b of the distal end cover 54 form these illumination optical system hole portions 72, the observation optical system hole portion 74, the channel hole portion 76, and the air supply/water supply hole portion 78 in cooperation with each other. On the distal end surface 54a side of the air supply/water supply hole portion 78 of the distal end cover 54, an annular protruding portion (an engagement portion) 78a having an inside diameter that is larger than an outside diameter of each of the later-described core member 84 and the coupling portion 86 of the nozzle 28a and smaller than the cover member 82 is formed to protrude inward along a radial direction.

Figure 4:
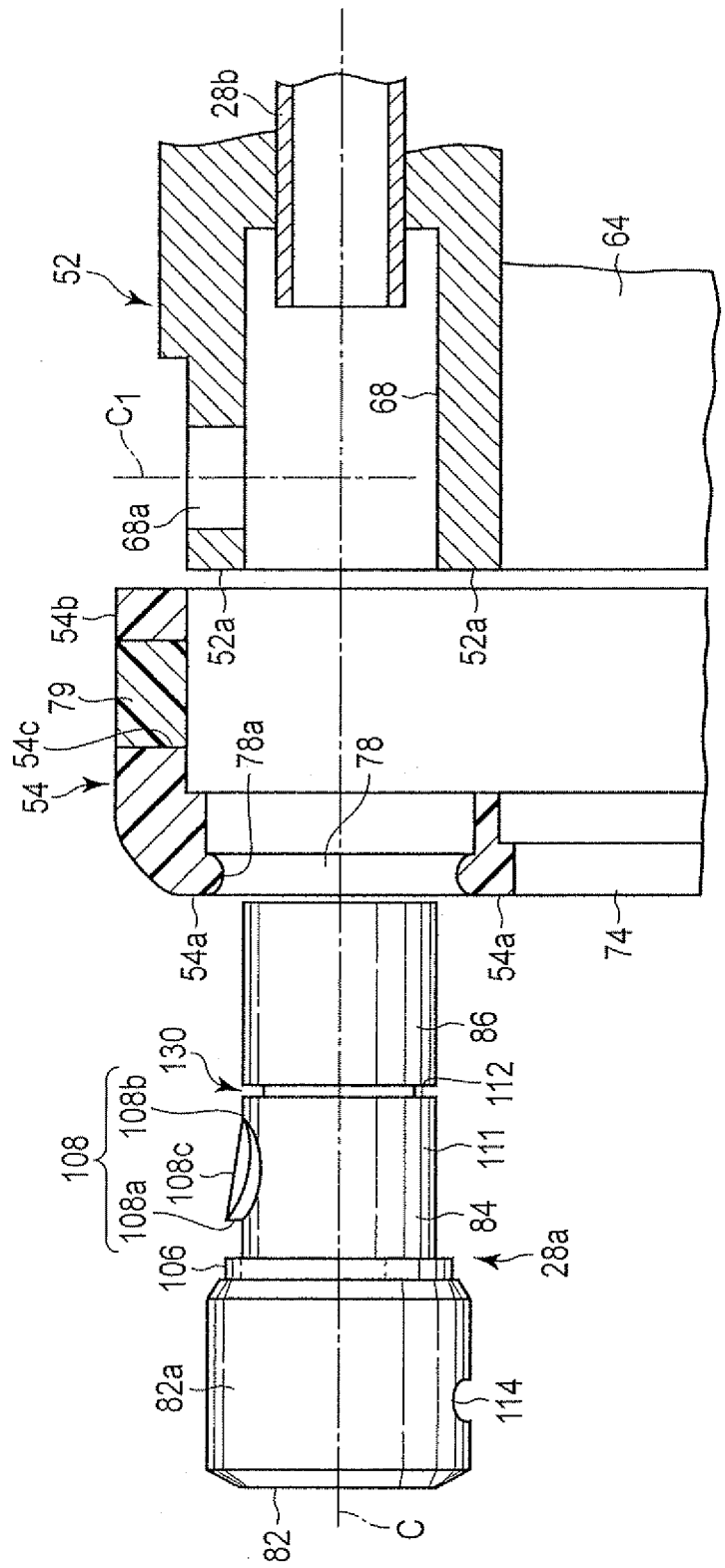
FIG. 4 is an exploded view of the distal end hard portion of the insertion portion of the endoscope according to the first embodiment and also a schematic partial cross-sectional view showing a distal end portion main body and a distal end cover of the distal end hard portion.

As shown in FIG. 4, for example, a circular opening 54c is formed in the side surface 54b of the distal end cover 54. The opening 54c is filled with a filling member 79 made of a material that is softly deformable with respect to the distal end cover 54, and a watertight state is formed. As the filling member 79, for example, silicone rubber having heat-resisting properties, insulation properties, acid-resisting properties, base-resisting properties, and others is used. The shape of each of the opening 54c and the filling member 79 is not restricted to the circular shape, and various shapes are allowed. Furthermore, although a diameter of the opening 54c seems equal to a diameter of the through hole 68a in FIG. 4 and FIG. 5A, reducing the diameter of the opening 54c to be smaller than that of the through hole 68a is also preferable. The filling member 79 does not come off the distal end cover 54 during use of the endoscope 10, and it can be removed from the opening 54c after use. When the filling member 79 is removed from the opening 54c, the opening 54c can be refilled with this material.

It is to be noted that, when the distal end cover 54 is fixed to the distal end portion main body 52, each hole portion of the distal end portion main body 52 and each hole portion of the distal end cover 54 are placed on the same axis. That is, the air supply/water supply hole portion 68 of the distal end portion main body 52 and the air supply/water supply hole portion 78 of the distal end cover 54 are placed on the same axis, and the observation optical system hole portion 64 of the distal end portion main body 52 and the observation optical system hole portion 74 of the distal end cover 54 are placed on the same axis.

The nozzle 28a shown in FIG. 3A to FIG. 3E includes a cover member (a head portion) 82 arranged to protrude with respect to the distal end surface 54a of the distal end cover 54 (the distal end surface 54a of the distal end hard portion 42), a core member (a base material) 84, and a coupling portion (a movement regulating portion; an axial movement regulating portion; and a circumferential movement regulating portion) 86 which is arranged in the distal end portion main body 52 and coupled with a distal end of the air supply/water supply pipe 28b.

The nozzle 28a is formed by, e.g., two-color molding, the cover member 82 is thermally fused and integrated with one end of the core member 84 on the outer side, and the coupling portion 86 is thermally fused and integrated with the other end of the same. As each of the cover member 82, the core member 84, and the coupling portion 86, a material having excellent water repellency and good sliding properties with respect to, e.g., a living body is used, and using, e.g., olefin-base thermoplastic elastomer is preferable. Besides, for example, a styrene-based or polyester-based resin material can be used.

It is to be noted that, when a harder material than those of the cover member 82 and the coupling portion 86 is used for the core member 84 and adjusted and the nozzle 28a is formed by the two-color molding, the cover member 82 and the coupling portion 86 have the same hardness. For example, when olefin-based elastomer is used for each of the cover member 82, the core member 84, and the coupling portion 86, using polypropylene for the core member 84 enables these members to have different degrees of hardness. Besides, it is also preferable to use, e.g., an ABS resin for the core member 84 which is a harder member than the cover member 82 and the coupling portion 86 and to use polyester-based elastomer for the cover member 82 and the coupling portion 86 which are softer members.

Furthermore, the core member 84, the cover member 82, and the coupling portion 86 may have hardness that the core member 84, the cover member 82, and the coupling portion 86 are pinched with fingers and a person who pinched can easily feel elastic deformation, or these members may formed to be slightly harder. In particular, the core member 84 must have the hardness that allows insertion into the hole portions 68 and 78 of the distal end hard portion 42 without buckling. For example, it is preferable for Type D durometer hardness of the core member 84 to be, e.g., 30 or above and Type A durometer hardness of each of the cover member 82 and the coupling portion 86 to be, e.g., approximately 10 to 50.

The cover member 82 of the nozzle 28a protrudes with respect to the distal end surface 54a of the distal end cover 54. Therefore, external force is applied to the cover member 82 so that the cover member 82 (and the core member 84) of the nozzle 28a can be squashed and deformed in some circumstances. In such a case, since each of the cover member 82 and the core member 84 is made of a resin material, the cover member 82 can be squashed and deformed, but the resin member is adjusted so that the cover member 82 can be recovered to its original shape by its own elastic force, namely, the cover member 82 has self-recovery properties. On the other hand, the core member 84 is formed to be hard so that deformation can be suppressed as compared with the cover member 82. Therefore, although the cover member 82 is squashed and deformed when external force is applied to the cover member 82, the core member 84 on the inner side of the cover member 82 is hardly squashed and deformed, and hence the deformation of the cover member 82 can be suppressed as compared with a situation where the core member 84 is largely squashed and deformed. Therefore, it can be said that, in the relationship between the cover member 82 and the core member 84, the cover member 82 (and the core member 84) is assuredly recovered to its original shape even though an impact load is applied to the cover member 82 and the cover member 82 (and the core member 84) is deformed, and hence the nozzle 28a has high resistance against the impact load.

In regard to the hardness of each of the cover member 82 and the coupling portion 86, these members are formed to be more flexible than the distal end cover 54 of the distal end hard portion 42. Therefore, when the nozzle 28a is arranged in the air supply/water supply hole portion 78, the protruding portion 78a pushes an outer peripheral surface 82a of the cover member 82 because of the relationship between the protruding portion 78a of the air supply/water supply hole portion 78 in the distal end cover 54 and the later-described outer peripheral surface (an annular portion) 82a of the cover member 82. Therefore, a gas and a liquid can be prevented from flowing between the distal end surface 54a of the distal end cover 54 and the distal end surface 52a of the distal end portion main body 52 from the distal end surface 54a of the distal end cover 54 through the air supply/water supply hole portion 78. That is, when the protruding portion 78a of the air supply/water supply hole portion 78 of the distal end cover 54 engages with the outer peripheral surface 82a of the cover member 82, air-tightness and water-tightness in the endoscope 10 (in the insertion portion 12) can be assured. In case of medical purposes, although cleaning, disinfection, and sterilization are carried out after use of the endoscope 10, the air-tightness and the water-tightness can be likewise assured during these operations.

It is to be noted that the core member 84, the cover member 82, and the coupling portion 86 are not restricted to the above-described materials, and they can be molded by using appropriate materials. In this case, when the hardness is adjusted, appropriate materials can be selected. As will be described later, a metal material may be used for the core member 84.

The cover member 82 is formed into a substantially cylindrical shape with one end being closed, and an opening 92 which is arranged at a position protruding from the distal end surface 54a and from which a fluid such as a liquid or a gas is discharged is formed in the substantially cylindrical outer peripheral surface 82a provided at a position close to the closed one end. As shown in FIG. 3A, FIG. 3B, FIG. 3D, and FIG. 3E, the opening 92 is formed as a slotted hole which is long in a direction orthogonal to a central axis C direction of the cover member 82 which is the central axis C of the nozzle 28a. It is preferable for a longitudinal direction of the slotted hole of the opening 92 to be parallel or substantially parallel to the distal end surface of the distal end cover 54. It is to be noted that, when the shape of the opening 92 is appropriately changed, a discharging state of a liquid/gas flowing from the nozzle 28a toward the observation window 24a can be changed. Moreover, although not shown, a top plan of the cover member 82 has, e.g., a circular shape.

The core member 84 is formed into a substantially cylindrical shape with one end being closed. A flow path 102, an opening 104, the flange 106, the boss portion 108, and an annular concave portion 110 are formed to the core member 84. Although integrally forming the core member 84, the flange portion 106, and the boss portion 108 is preferable, separately forming these members is also preferable.

The flow path 102 is continuously formed from the other end (the coupling portion 86 side) toward one end (the cover member 82 side) of the substantially cylindrical inner side of the core member 84. The opening 104 is formed at a position which is provided on a substantially cylindrical side surface of the core member 84, communicates with the flow path 102, and is close to the closed one end of the core member 84. The opening 104 of the core member 84 is arranged concentrically with the opening 92 of the cover member 82. Additionally, in the nozzle 28a having the cover member 82 integrally molded with the core member 84, the opening 104 of the cover member 82 is integrated with the opening 92 of the core member 84, and these openings 104 and 92 form one nozzle opening 114. Therefore, a fluid flowing from the other end toward the one end of the core member 84 through the flow path 102 can be discharged to the outside of the nozzle 28a via the nozzle opening 114.

In addition, it is preferable for the one end side of the flow path 102 close to the nozzle opening 114 to have a cross-sectional area smaller than that of the other end side of the same. When such a shape is adopted, the fluid (a liquid/gas) can be energetically discharged from the nozzle opening 114.

The flange (the movement regulating portion; the axial movement regulating portion; the circumferential movement regulating portion) 106 of the core member 84 is formed into, e.g., an annular shape on an outer peripheral surface 111 of the core member 84 on the other end side of the opening 104 and abuts on the distal end surface 52a of the distal end portion main body 52. Therefore, the flange 106 is used for positioning an axial position of the core member 84, i.e., an axial position of the nozzle 28a with respect to the distal end surface 52a of the distal end portion main body 52. Further, since the flange 106 has the annular shape and abuts on the distal end surface 52a of the distal end portion main body 52, the nozzle 28a can be prevented from tilting with respect to the central axis C of the air supply/water supply hole portions 68 and 78.

In this embodiment, the boss portion (the engagement portion; the movement regulating portion; the axial movement regulating portion; the circumferential movement regulating portion) 108 is integrally formed to protrude with respect to the outer peripheral surface 111 of the core member 84 on the other end side of the core member 84 away from the flange 106. That is, the boss portion 108 protrudes in the direction orthogonal to the axial direction (the central axis C) of the core member 84. When the boss portion 108 is engaged with the through hole 68a of the distal end portion main body 52, the axial position of the core member 84, i.e., the axial position of the nozzle 28a can be positioned with respect to the distal end portion main body 52, and a circumferential position of the core member 84, i.e., a circumferential position of the nozzle 28a can be positioned with respect to the distal end portion main body 52. The boss portion 108 has a smaller amount of protrusion of an edge portion 108b on the other outermost end side (the coupling portion 86 side) toward the outer peripheral surface 111 of the core member 84 than that of an edge portion 108a on the one outermost end side (the cover member 82 side), and a surface of the boss portion 108 away from the outer peripheral surface 111 of the core member 84 is formed as an inclined surface 108c. Furthermore, in a left side elevation shown in FIG. 3B and a cross-sectional view shown in FIG. 3D, the one edge portion 108a of the boss portion 108 on the one outermost end side is formed to be orthogonal or substantially orthogonal to the outer peripheral surface 111 of the core member 84. It is to be noted that an angle formed between the outer peripheral surface 111 on the one end side of the edge portion 108a of the core member 84 and the edge portion 108a is not restricted to be orthogonal or substantially orthogonal, and it may be an acute angle. When the angle is an acute angle, the central axis C1 of the through hole 68a may be orthogonal or substantially orthogonal to the axial direction of the insertion portion 12 (the central axis C of the nozzle 28a), and this angle may be also preferably, e.g., an acute angle equal to an acute angle formed between the outer peripheral surface 111 on the one end side of the edge portion 108a of the core member 84 and the edge portion 108a.

Since the boss portion 108 includes the inclined surface 108c, when the core member 84 is inserted into the distal end portion main body 52, this member can be easily inserted because of elastic deformation of the core member 84, and the boss portion 108 can be engaged with the through hole 68a of the distal end portion main body 52. At this time, the edge portion 108b on the other outermost end side of the boss portion 108 also slightly protrudes with respect to the outer peripheral surface 111 of the core member 84 as shown in FIG. 5B. Therefore, the entire boss portion 108 protruding with respect to the outer peripheral surface 111 of the core member 84 can be arranged in the through hole 68a of the distal end portion main body 52, and the outer peripheral surface 111 of the core member 84 can be appressed against the inside of the air supply/water supply hole portion 68. It is to be noted that forming the boss portion 108 to be slightly smaller than the through hole 68a is preferable. In this case, the outer peripheral surface 111 of the boss portion 108 that is continuous with the outer peripheral surface 111 of the core member 84 can be in close contact with the inner peripheral surface of the through hole 68a, the boss portion 108 elastically deforms outward in the radial direction (which is the central axis C1 direction and also a direction to get closer to the side surface 54b of the distal end cover 54) with respect to the central axis C of the core member 84, and hence an area of the boss portion 108 that is appressed against the inner peripheral surface of the through hole 68a can be increased. Therefore, the core member 84 can be firmly held with respect to the distal end portion main body 52.

On the other hand, in case of pulling out the core member 84, since the edge portion 108a that is close to the one outermost end side of the boss portion 108 is caught by the through hole 68a of the distal end portion main body 52, the edge portion 108 is hardly removed and functions as a stopper. Therefore, external force must be applied so that the inclined surface 108c of the boss portion 108 can elastically deform inward along the radial direction (which is the central axis C1 direction and also a direction to get away from the side surface 54b of the distal end cover 54) with respect to the central axis C of the core member 84, and the boss portion 108 must be disengaged from the through hole 68a.

Figure 5A:
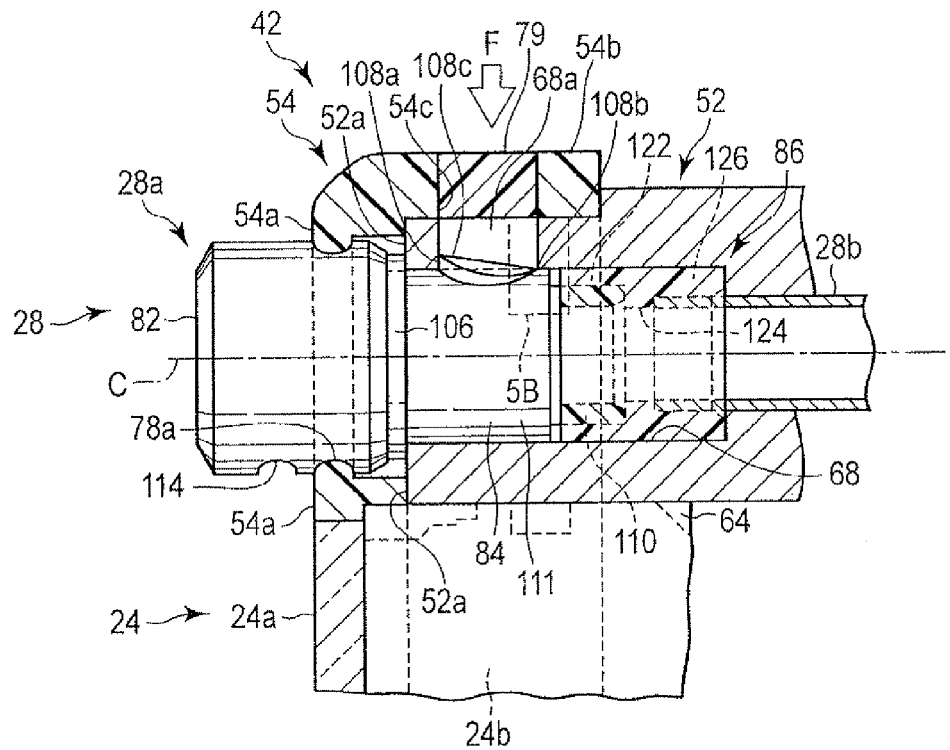
FIG. 5A is a partial cross-sectional view of the distal end hard portion of the insertion portion of the endoscope according to the first embodiment.
Figure 5B:
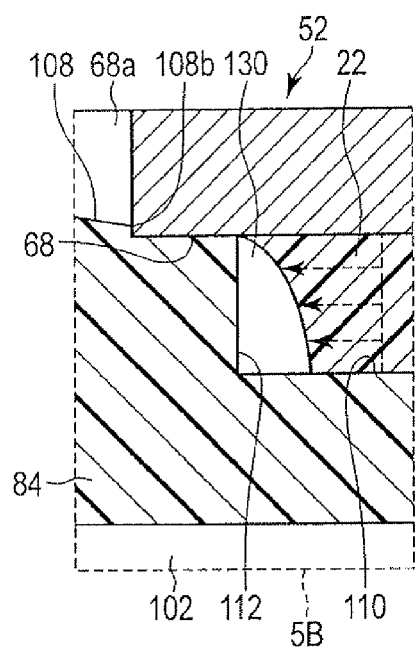
FIG. 5B is an enlarged cross-sectional view of a position denoted by reference sign 5B in FIG. 5A.
Figure 6A:
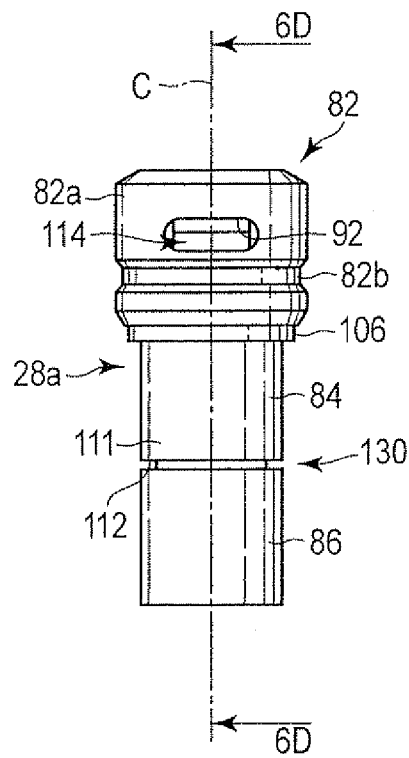
FIG. 6A is a front view showing a nozzle attached to a distal end hard portion of an insertion portion of an endoscope according to a first modification of the first embodiment.
Figure 6B:
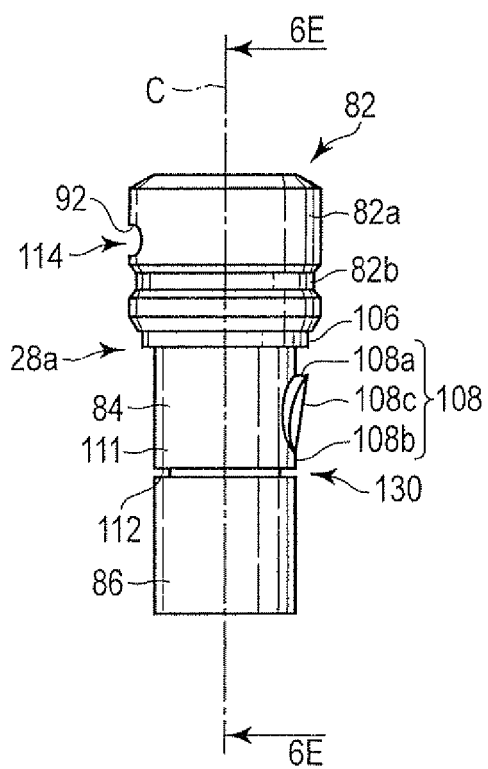
FIG. 6B is a right side view showing the nozzle attached to the distal end hard portion of the insertion portion of the endoscope according to the first modification of the first embodiment.
Figure 6C:
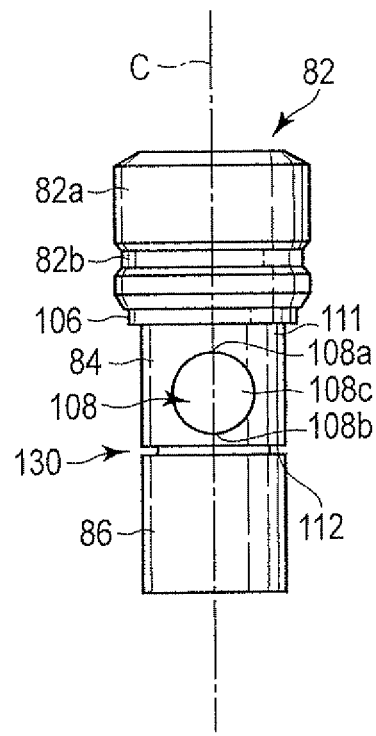
FIG. 6C is a back view showing the nozzle attached to the distal end hard portion of the insertion portion according to the first modification of the first embodiment.
Figure 6D:
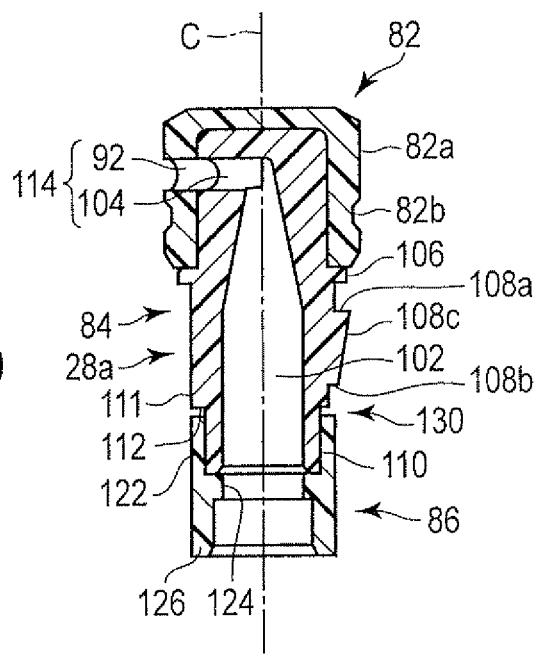
FIG. 6D is a cross-sectional view which shows the nozzle attached to the distal end hared portion of the insertion portion of the endoscope according to the first modification of the first embodiment, and is taken along a line 6D-6D in FIG. 6A.
Figure 6E:
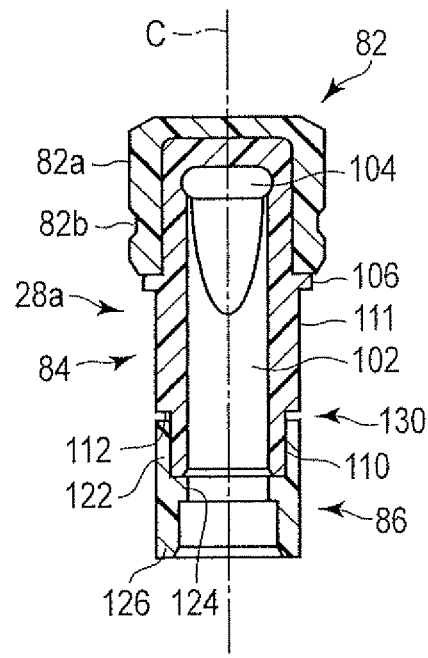
FIG. 6E is a cross-sectional view which shows the nozzle attached to the distal end hard portion of the insertion portion of the endoscope according to the first modification of the first embodiment, and is taken along a line 6E-6E in FIG. 6B.
Figure 7A:
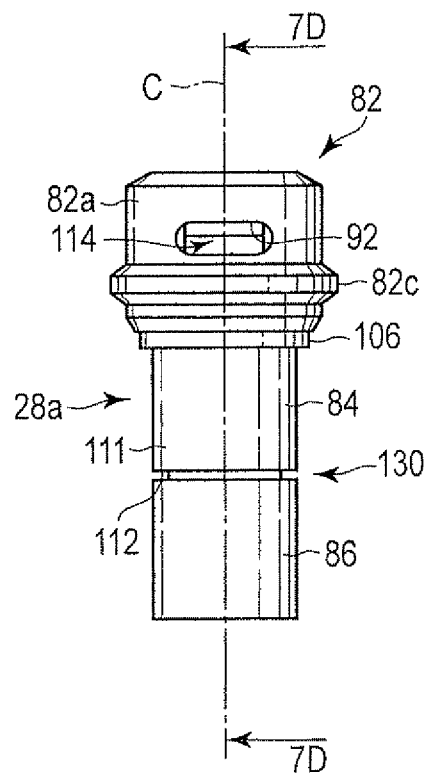
FIG. 7A is a front view showing a nozzle attached to a distal end hard portion of an insertion portion of an endoscope according to a second modification of the first embodiment.
Figure 7B:
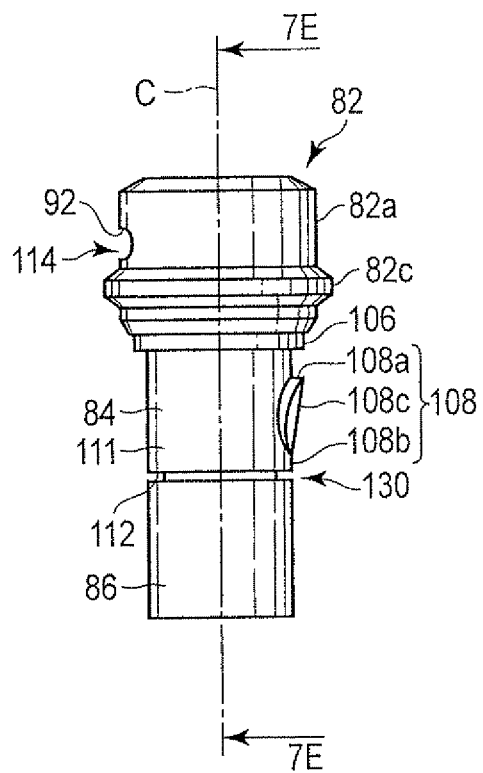
FIG. 7B is a right side view showing the nozzle attached to the distal end hard portion of the insertion portion of the endoscope according to the second modification of the first embodiment.
Figure 7C:
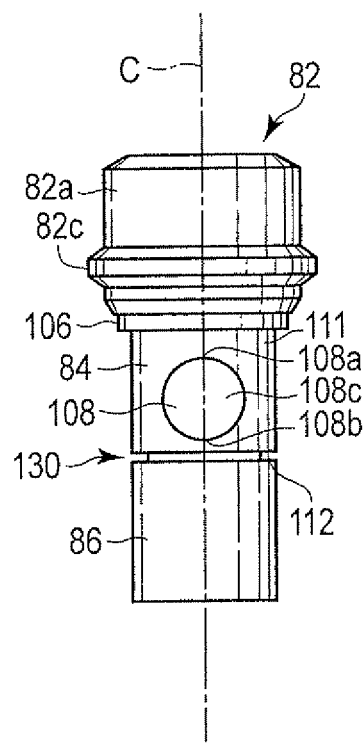
FIG. 7C is a back view showing the nozzle attached to the distal end hard portion of the insertion portion of the endoscope according to the second modification of the first embodiment.
Figure 7D:
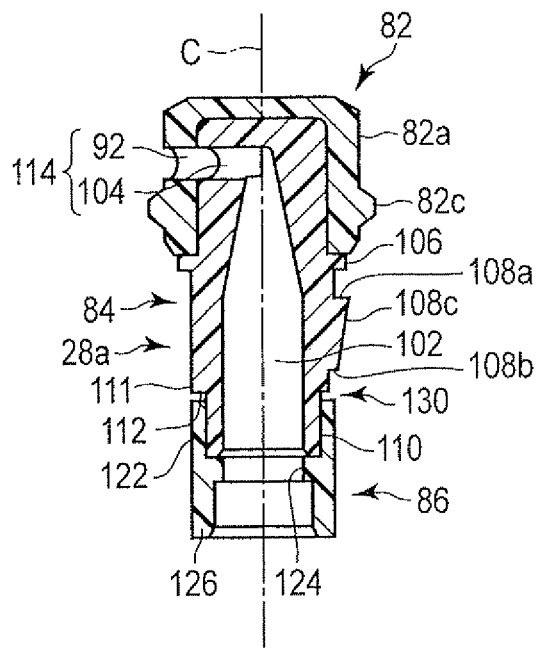
FIG. 7D is a cross-sectional view which shows the nozzle attached to the distal end hard portion of the insertion portion of the endoscope according to the second modification of the first embodiment, and is taken along a line 7D-7D in FIG. 7A.
Figure 7E:
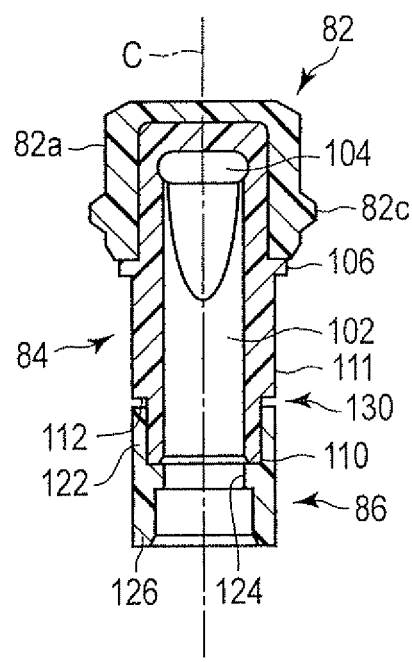
FIG. 7E is a cross-sectional view which shows the nozzle attached to the distal end hard portion of the insertion portion of the endoscope according to the second modification of the first embodiment, and is taken along a line 7E-7E in FIG. 7B.

It is to be noted that the circumferential position of the boss portion 108 is preferably arranged on a side which is close to the substantially cylindrical side surface of the distal end cover 54 in a state that the distal end hard portion 42 is attached to the nozzle 28a as shown in FIG. 5A. That is because, at a time of replacing the nozzle 28a, in order to disengage the boss portion 108 from the through hole 68a of the distal end portion main body 52, the filling member 79 filling the opening 54c in the side surface 54b from the outer side of the distal end cover 54 must be pressed with force F so that the boss portion 108 can be disengaged from the through hole 68a, or the filling member 79 must be removed from the distal end cover 54 and the opening 54c is formed so that the boss portion 108 can be disengaged from the through hole 68a. In regard to the positional relationship between the boss portion 108 of the nozzle 28a and the nozzle opening 114, although depending on the arrangement of the observation window 24a (the observation optical system 24), these members are preferably relatively provided on the outer peripheral surface on the opposite sides with respect to the central axis C of the nozzle 28a.

It is also preferable to fill the through hole 68a between the boss portion 108 and the distal end cover 54 with a harder resin material than the boss portion 108. That is, arranging the resin material between the filling member 79 and the boss portion 108 is also preferable. Then, when the force F is applied to the filling member 79 from the outer side of the distal end cover 54, the force F can be easily transmitted to the boss portion 108 at the time of pressing the boss portion 108 of the core member 84 with this resin material.

The annular concave portion 110 of the core member 84 is formed on the outer peripheral surface 111 of the core member 84 on the other end side of the core member 84 away from the boss portion 108 so that the coupling portion 86 can be integrally molded. In the core member 84, an inner peripheral surface of a portion where the boss portion 108 is formed and an inner peripheral surface of a portion where the annular concave portion 110 is formed, i.e., the flow path 102 is flush, a wall thickness of the portion where the boss portion 108 is formed and a wall thickness of the portion where the annular concave portion 110 is formed are substantially constant, respectively. Further, the wall thickness of the portion where the boss portion 108 is formed is larger than the wall thickness of the portion where the annular concave portion 110 is formed, and a step 112 is formed by using the annular concave portion 110 at a boundary between outer peripheral surfaces of these portions.

The substantially cylindrical coupling portion 86 is arranged at the other end of the core member 84. The coupling portion 86 includes: a distal end-side cylindrical portion (one end-side cylindrical portion) integrated with the outer peripheral surface of the annular concave portion 110 of the core member 84 by fusion; a flange 124 which is substantially annularly formed on the inner peripheral surface of the coupling portion 86 and fused in contact with a rear end of the core member 84 and on which a distal end of the air supply/water supply pipe 28b abuts; and a proximal end-side cylindrical portion (the other end-side cylindrical portion) 126 which guides the air supply/water supply pipe 28b toward the flange 124 when the distal end of the air supply/water supply pipe 28b abuts on the flange 124.

An inner peripheral surface of the proximal end-side cylindrical portion 126 on a proximal end is chamfered and formed to facilitate insertion of the distal end of the air supply/water supply pipe 28b to the flange 124. In regard to an inner peripheral surface of the coupling portion 86, it is preferable for an inside diameter (an inside diameter of the proximal end-side cylindrical portion 126) of a portion from a position of the flange 124 to the proximal end of the proximal end-side cylindrical portion 126 to be slightly smaller than an outside diameter of the air supply/water supply pipe 28b. At this time, since the inside diameter of the chamfered inner peripheral surface of the proximal end-side cylindrical portion 126 at the proximal end is formed to equal to or slightly larger than the outside diameter of the air supply/water supply pipe 28b in order to guide the air supply/water supply pipe 28b toward the flange 124. When such a configuration is adopted, the distal end of the air supply/water supply pipe 28b can be readily inserted into the coupling portion 86, the inner peripheral surface of the proximal end-side cylindrical portion 126 is appressed against the outer peripheral surface of the air supply/water supply pipe 28b, and hence the air supply/water supply pipe 28b from being removed from the coupling portion during use of the endoscope 10. Further, since the outer peripheral surface of the air supply/water supply pipe 28b is appressed against the inner peripheral surface of the proximal end-side cylindrical portion 126, a fluid such as a liquid or a gas can be prevented from leaking from a position between the outer peripheral surface of the air supply/water supply pipe 28b and the inner peripheral surface of the proximal end-side cylindrical portion 126.

A gap (a space) 130 is annularly formed between the distal end of the coupling portion 86 and the step 112 of the core member 84. As shown in FIG. 5B, this gap 130 functions as a clearance portion of the coupling portion 86 which is made of a resin material when the nozzle 28a is arranged in the distal end portion main body 52 and elastically deformed. Although an axial length of the gap 130 varies depending on, e.g., a size of the nozzle 28a, hardness or a wall thickness of the core member 84, and hardness or a wall thickness of the coupling portion 86, the gap of, e.g., approximately several mm can suffice.

As shown in FIG. 3A to FIG. 3E, the outer edge portion of the flange 106 of the core member 84 is placed at a position closer to the central axis C of the nozzle 28a than the outer peripheral surface 82a of the cover member 82. That is, an outside diameter of the cover member 82 is larger than an outside diameter of the flange 106 of the core member 84. Since the cover member 82 is more flexible than the core member 84 and also more flexible than the distal end cover 54 of the distal end hard portion 42, it easily deforms with respect to the core member 84 or the distal end cover 54. Furthermore, since the rear end of the cover member 82 is appressed against the one end side of the flange 106 of the core member 84 by fusion, the cover member 82 can be prevented from being removed from the core member 84 even though force is applied.

Moreover, in the nozzle 28a having the coupling portion 86 integrated with the core member 84, since the other end of the core member 84 is completely appressed against the flange 124 of the coupling portion 86, a fluid is prevented from flowing out from a position between the other end of the core member 84 and the flange 124 of the coupling portion 86. Since the coupling portion 86 is more flexible than the core member 84 and also more flexible than the distal end portion main body 52, the coupling portion 86 readily deforms with respect to the core member 84 or the distal end portion main body 52.

A function of the endoscope 10 according to this embodiment will now be described. Here, a description will be given as to a case of replacing of the air supply/water supply nozzle 28a arranged to be inserted in the air supply/water supply hole portions 68 and 78 of the distal end hard portion 42 of the insertion portion 12 in the endoscope 10.

The filling member 79 in the side surface 54b of the distal end cover 54 facing the through hole 68a of the distal end portion main body 52 of the distal end hard portion 42 is pressed by using, e.g., a non-illustrated pin. Therefore, the filling member 79 made of silicone rubber or the like deforms, and the boss portion 108 of the nozzle 28a is pressed via the through hole 68a of the distal end portion main body 52. Alternatively, the filling member 79 is removed from the side surface 54b of the distal end cover 54 placed at the position where it faces the boss portion 108 of the nozzle 28a, and the boss portion 108 is directly pressed by using, e.g., a non-illustrated pin via the opening 54c. Therefore, the boss portion 108 of the core member 84 elastically deforms, and the boss portion 108 is disengaged from the through hole 68a of the distal end portion main body 52. At this time, the cover member 82 of the nozzle 28a is pinched and pulled, and the edge portion 108a provided on the one outermost end side (the cover member 82 side) of the boss portion 108 is thereby moved to the one end side of the nozzle 28a. That is, the core member 84 moves toward the distal end side of the insertion portion 12.

Although the coupling portion 86 is fixed to the air supply/water supply hole portion 68 of the distal end portion main body 52, the coupling portion 86 is integrated with the core member 84 of the nozzle 28a, and hence the coupling portion 86 moves as the boss portion 108 moves. Therefore, when the boss portion 108 is pressed, the engagement state of the coupling portion 86 with respect to the air supply/water supply hole portion 68 of the distal end portion main body 52 that the outer peripheral surface of the coupling portion 86 is appressed against the air supply/water supply hole portion 68 is released.

When the core member 84 moves toward the distal end side of the insertion portion 12, the cover member 82 is pushed out together with the core member 84 against frictional force between the outer peripheral surface (the engagement portion; the movement regulating portion; the axial movement regulating portion; and the circumferential movement regulating portion) of the cover member 82 of the nozzle 28a and the protruding portion 78a of the distal end cover 54. Therefore, the outer peripheral surface 82a of the cover member 82 of the nozzle 28a is also disengaged from the protruding portion 78a of the distal end cover 54.

At the rear end of the coupling portion 86 of the nozzle 28a, the distal end of the air supply/water supply pipe 28b fixed to or integrally formed with the distal end portion main body 52 is locked by friction. Therefore, when the core member 84 moves toward the distal end side of the insertion portion 12, the coupling portion 86 of the air supply/water supply nozzle 28a moves and separates from the air supply/water supply pipe 28b.

Further, since the outside diameter of each of the core member 84 and the coupling portion 86 is smaller than the inside diameter of the protruding portion 78a, the nozzle 28a can be removed from the distal end portion main body 52 and the distal end cover 54.

It is to be noted that, when the opening 54c pierced in the side surface 54b of the distal end cover 54 is formed, the distal end cover 54 itself can be removed from the distal end portion main body 52 and replaced. In case of replacing the distal end cover 54, the new distal end cover 54 is fixed to the distal end portion main body 52 in such a manner that the hole portions 68 and 78 shown in FIG. 4A are arranged on the same axis and the hole portions 64 and 74 are arranged on the same axis.

The new nozzle 28a is prepared in place of the removed nozzle 28a.

The nozzle 28a is inserted from the coupling portion 86 into the hole portion 78a of the distal end cover 54 and the hole portion 68 of the distal end portion main body 52 in such a manner that the nozzle opening 114 of the nozzle 28a faces the observation window 24a.

The nozzle 28a is inserted from the proximal end side of the coupling portion 86 to the flange 124 and allowed to abut on the flange 124 with respect to the distal end of the air supply/water supply pipe 28b. At this time, since the outside diameter of the air supply/water supply pipe 28b is slightly larger than the inside diameter of the proximal end-side cylindrical portion 126 of the coupling portion 86, the proximal end-side cylindrical portion 126 of the coupling portion 86 elastically deforms, and adhesion is achieved by friction. Therefore, the outer peripheral surface of the distal end portion of the air supply/water supply pipe 28b and the inner peripheral surface of the proximal end-side cylindrical portion 126 are fixed, and the water-tightness and the air-tightness can be assured.

At this time, the boss portion 108 is inserted while abutting on the inner peripheral surface of the air supply/water supply hole portion 68 of the distal end portion main body 52. Since the core member 84 can elastically deform and the boss portion 108 of the core member 84 is formed into the inclined surface whose wall thickness is small on the lower side and larger on the upper side in FIG. 3B and FIG. 3D, the core member 84 of the nozzle 28a can be easily inserted without being caught at the time of inserting the core member 84 into the hole portion 68 of the distal end portion main body 52. Furthermore, when the boss portion 108 faces the through hole 68a of the distal end portion main body 52, the core member 84 and the boss portion 108 elastically deform, whereby the boss portion 108 is put into the through hole 68a of the distal end portion main body 52. At this time, when the boss portion 108 is more harder, whether the boss portion 108 is successfully engaged with the through hole 68a can be recognized through the touch of a hand. In this manner, the boss portion 108 is fitted in (engaged with) the through hole 68a. Therefore, the nozzle 28a is held in a state that the axial direction and the circumferential direction are determined with respect to the distal end portion main body 52.

In this manner, when the boss portion 108 is fitted in the through hole 68a, the flange 106 of the core member 84 is allowed to abut on the distal end surface 52a of the distal end portion main body 52. Therefore, aside from the boss portion 108, the nozzle 28a is prevented from moving toward the proximal end side of the insertion portion 12. That is, the flange 106 defines the axial position of the nozzle 28a.

Since the coupling portion 86 is made of a material softer than that of the core member 84, it considerably deforms as compared with the core member 84. Therefore, when the nozzle 28a is arranged in the distal end hard portion 42, the gap 130 shown in FIG. 5B moves from a portion indicated by a broken line toward the step 112. That is, when the nozzle 28a is arranged in the air supply/water supply hole portion 68 of the distal end portion main body 52, the wall thickness of the outer peripheral surface of the coupling portion 86 is reduced due to elastic deformation, and this outer peripheral surface is appressed against the inner peripheral surface of the air supply/water supply hole portion 68 of the distal end portion main body 52 by self-recovery force (reaction force with respect to deformation of the coupling portion 86) equal to that of the cover member 82 that is made of the same material. Therefore, the other end side of the nozzle 28a is firmly held and achieving water-tightness with respect to the distal end portion main body 52. At this time, the coupling portion 86 engages with the inner peripheral surface of the air supply/water supply hole portion 68 in the axial direction and the circumferential direction.

The annular protruding portion 78a of the hole portion 78 in the distal end cover 54 is used to press the outer peripheral surface 82a of the cover member 82 of the nozzle 28a in an annular pattern. Since the cover member 82 itself has the self-recovery force, the annular protruding portion 78a of the distal end cover 54 receives the reaction force from the outer peripheral surface 82a of the cover member 82. Therefore, the appressed state and the fixed state between the protruding portion 78a and the outer peripheral surface 82a of the cover member 82 can be improved. Therefore, when the outer peripheral surface 82a of the cover member 82 is pressed by the protruding portion 78a, the air-tightness and the water-tightness in the insertion portion 12 can be assured, and a state that the position of the nozzle 28a is set out with respect to the distal end hard portion 42 can be maintained. At this time, movement of the outer peripheral surface 82a of the cover member 82 along the axial direction with respect to the protruding portion 78a as the inner peripheral surface of the air supply/water supply hole portion 78 is regulated, and movement of the same in the circumferential direction is regulated. Therefore, even when force is applied from the distal end side toward the proximal end side of the nozzle 28a, i.e., when force is applied to squash the cover member 82, the nozzle 28a can be prevented from being moved to the proximal end side. Therefore, the nozzle opening 114 is always provided on the distal end side of the distal end surface 54a of the distal end cover 54, and a liquid or a gas can be discharged from the nozzle opening 114. That is, the nozzle 28a can constantly exercise its functions while being attached to the distal end hard portion 42.

As described above, according to this embodiment, the following effects can be obtained.

At a time of attaching the nozzle 28a to the distal end hard portion 42, determining a direction of the nozzle 28a with respect to the distal end hard portion 42 and inserting the nozzle 28a can suffice, a troublesome operation such as heating the nozzle 28a or the distal end hard portion 42 is not required, and hence an attachment operation can be easily carried out in a short time. At a time of removing the nozzle 28a from the distal end hard portion 42, the nozzle 28a can be removed by just elastically deforming the filling member 79 in the side surface 54b of the distal end cover 54 or disengaging the nozzle 28a from the distal end portion main body 52 through the opening 54c formed in the side surface 54b of the distal end cover 54 and then pulling the nozzle 28a, and hence the nozzle 28a can be also easily removed from the distal end hard portion 42. Therefore, using the self-restoration properties, i.e., the elastic force of the nozzle 28a enables fixation to/removal from the distal end hard portion 42, whereby attachability/detachability at the time of attaching/detaching the nozzle 28a to/from the distal end rigid portion 42 can be improved.

Furthermore, when the nozzle 28a is made of the resin material alone, processing is easier than that in a case of using a metal material, and a weight can be reduced.

In a state that the boss portion 108 protruding in the direction orthogonal to the axial direction of the core member 84 is fitted in the through hole 68a in the distal end portion main body 52, the nozzle 28a is held, and hence the axial position and the circumferential position of the nozzle 28a with respect to the distal end portion main body 52 can be assuredly held by using the boss portion 108.

Since a protruding length of the edge portion 108a on the one end side (the cover member 82 side) of the boss portion 108 with respect to the outer peripheral surface 111 of the core member 84 is large and a protruding length of the edge portion 108b on the other end side (the coupling portion 86 side) is smaller than that of the edge portion 108a, the nozzle 28a can be easily inserted into the distal end cover 54 and the distal end portion main body 52, and unintentional removal can be avoided. On the other hand, at a time of removing the nozzle 28a from the distal end hard portion 42 and replacing it, when the boss portion 108 is disengaged from the through hole 68a, the protruding length of the boss portion 108 with respect to the outer peripheral surface 111 of the core member 84 is gradually reduced from the one end side toward the other end side because of the inclination of the inclined surface 108c of the boss portion 108, and hence the nozzle 28a can be easily removed from the air supply/water supply hole portion 68 of the distal end main body 52 by pulling the nozzle 28a.

Since the nozzle 28a is held in a state that the annular flange 106 of the core member 84 abuts on the distal end surface 52a of the distal end portion main body 52, using the flange 106 of the core member 84 enables holding the axial position of the nozzle 28a with respect to the distal end portion main body 52.

Since the outer peripheral surface of the coupling portion 86 of the nozzle 28a is appressed against the inner peripheral surface of the air supply/water supply hole portion 68 of the distal end portion main body 52 in an elastically deformed state, the axial position and the circumferential position of the nozzle 28a with respect to the distal and portion main body 52 can be held by the coupling portion 86.

As described above, in this embodiment, the movement of the nozzle 28a in the axial direction and the circumferential direction can be regulated between the distal end portion main body 52 of the distal end hard portion 42 and the core member 84 and the coupling portion 86 of the nozzle 28a and between the distal end cover 54 of the distal end hard portion 42 and the cover member 82. Moreover, in a state that the distal end of the insertion portion 12 in the endoscope 10 includes the nozzle 28a disposed thereto, even if force is applied to the nozzle 28a, the core member 84 avoids large deformation (squashing deformation) of the cover member 82, and hence the watertight and airtight state can be maintained between the nozzle 28a and the distal end hard portion 42. Therefore, the nozzle 28a can be prevented from unintentionally coming off the distal end of the insertion portion 12 during use of the endoscope 10.

It is to be noted that the description has been given as to the example where the boss portion 108 is integrally molded with the core member 84, but it is also preferable to form the boss portion 108 separately from the core member 84, make the boss portion 108 by using a resin material, and make the core member 84 by using a metal material such as a stainless steel material. In this case, the metal core member 84 is integrated with the resin cover member 82 and the coupling portion 86 by insert molding. As the resin material used for the boss portion 108, the cover member 82, and the coupling portion 86, for example, using well-known styrene-based elastomer or liquid silicone rubber having high adhesion performance with respect to the metal material is preferable. For example, when the core member 84 made of the stainless steel material, the boss portion 108, the cover member 82, and the coupling portion 86 are molded by using the styrene-based elastomer or liquid silicone rubber having high adhesion performance with respect to the metal material, the boss portion 108, the cover member 82, and the coupling portion 86 can be difficult to be delaminated from the core member 84. In this case, deformation of the core member 84 is suppressed, and hence the inside diameter of the air supply/water supply hole portion 68 of the distal end portion main body 52 is formed to be slightly larger than the outside diameter of the core member 84. Besides, like the above description, the air supply/water supply nozzle 28a can be used. Moreover, since the core member 84 is formed of the metal material, even if an object strongly strikes on the cover member 82 of the air supply/water supply nozzle 28a, the cover member 82 just elastically deforms, deformation of the core member 84 can be avoided. Therefore, a state that the nozzle opening 114 protrudes with respect to the distal end surface 54a of the distal end cover 54 can be maintained, and the functions of the nozzle 28a can be constantly exercised.

In this embodiment, although the description has been given as to the example where the outer peripheral surface 82a of the cover member 82 of the nozzle 28a engages with the protruding portion 78a of the hole portion 78 of the distal end cover 54, an adhesive or a resin material may be applied between these members. The application of the adhesive or the resin material can further enhance the water-tightness and the air-tightness between the nozzle 28a and the distal end cover 54, and the nozzle 28a can be further firmly fixed to the distal end cover 54.

It is to be noted that the endoscope 10 has been described as a medical device in this embodiment, the configuration of the insertion portion 12 including the nozzle 28a can be used for various purposes such as an industrial endoscope. For example, even the industrial endoscope has the same configuration including the insertion portion and the operation portion.

[First Modification]

A first modification of the first embodiment will now be described with reference to FIG. 6A to FIG. 6E. In this modification, like reference numerals denote members equal to those explained in the first embodiment, and a detailed description thereof will be omitted.

As shown in FIG. 6A to FIG. 6E, on the outer peripheral surface 82a of the cover member 82, an annular concave groove (an engagement portion; a movement regulating portion, an axial movement regulating portion; and a circumferential movement regulating portion) 82b in which the protruding portion 78a of the air supply/water supply hole portion 78 of the distal end cover 54 is fitted is formed. Therefore, when the concave groove 82b is formed on the outer peripheral surface 82a of the cover member 82, the concave groove 82b serves as a stopper, and the protruding portion 78a of the distal end cover 54 can be prevented from relatively moving in the axial direction of the cover member 82. Therefore, since the cover member 82 includes the concave groove 82b and a positional relationship between this concave groove 82b and the protruding portion 78a of the distal end cover 54 can be assuredly defined, a state that the nozzle 28a is stably disposed to the distal end hard portion 42 can be maintained.

It is to be noted that an inward protruding length of the protruding portion 78a in the radial direction with respect to the air supply/water supply hole portion 78 is preferably larger than that of the protruding portion 78a in the first embodiment, and a smaller inside diameter is desirable. For example, in case of using the same distal end portion main body 52 as the distal end portion main body 52 described in the first embodiment, the protruding portion 78a can be assuredly engaged with the concave groove 82b, and the water-tightness and the air-tightness can be exercised.

[Second Modification]

A second modification of the first embodiment will now be described with reference to FIG. 7A to FIG. 9. This modification is a modification of not only the first embodiment but also the first modification, and like reference numerals denote members equal to those explained in the first embodiment and the first modification, and a detailed description will be omitted.

This modification is an example of reversing a relationship between the concave groove 82b on the outer peripheral surface 82a of the cover member 82 of the nozzle 28a and the protruding portion 78a in the second embodiment.

Figure 8:
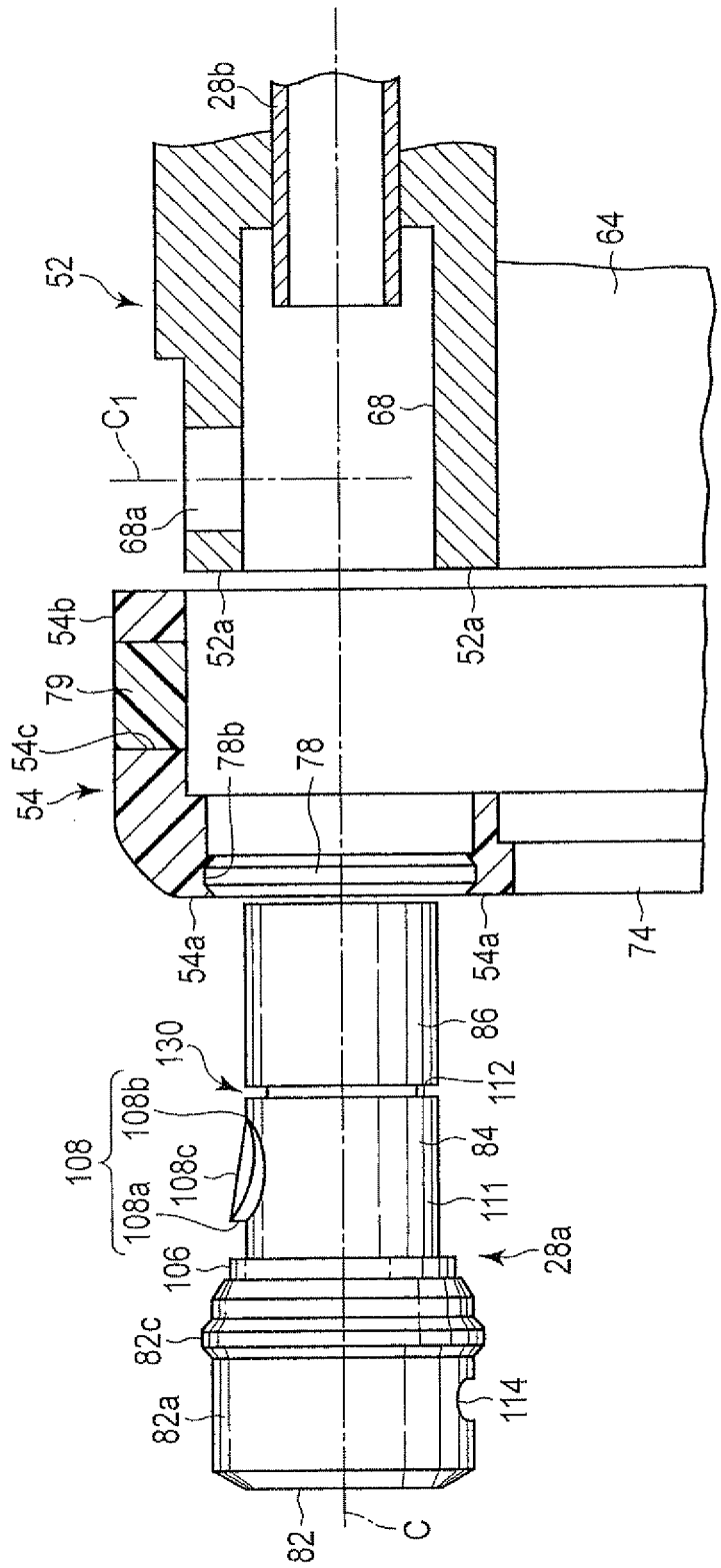
FIG. 8 is an exploded view of the distal end hard portion of the insertion portion of the endoscope according to the second modification of the first embodiment and is also a schematic partial cross-sectional view showing an air supply/water supply nozzle and a distal end portion main body and a distal end cover of the distal end hard portion.
Figure 9:
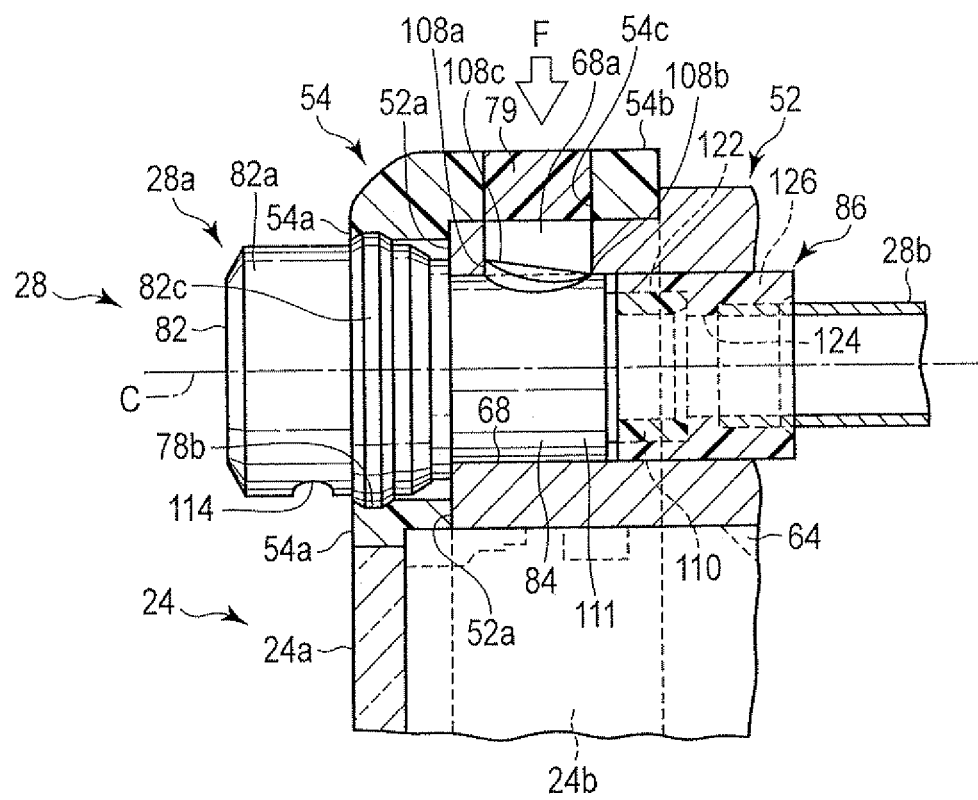
FIG. 9 is a partial cross-sectional view of the distal end hard portion of the insertion portion of the endoscope according to the second modification of the first embodiment.

As shown in FIG. 7A to FIG. 7E, on the outer peripheral surface 82a of the cover member 82 of the nozzle 28a, an annular convex portion (an engagement portion; a movement regulating portion; an axial movement regulating portion; and a circumferential movement regulating portion) 82c is formed in place of the concave groove 82b (see FIG. 6A to FIG. 6E). On the other hand, in the air supply/water supply hole portion 78 of the distal end cover 54, as shown in FIG. 8 and FIG. 9, a concave portion (an engagement portion) 78b is formed in place of the protruding portion 78a (see FIG. 4 and FIG. 5A).

When the convex portion 82c of the cover member 82 is fitted in the concave portion 78b of the distal end cover 54, like the first modification, the axial movement of the cover member 82 can be regulated with respect to the distal end cover 54. As just described, in this modification, since a state that the concave portion 78b of the distal end cover 54 is engaged with the convex portion 82c of the cover member 82 can be easily maintained, a position of the nozzle opening 114 with respect to the observation window 24a can be difficult to be displaced.

Since the cover member 82 of the nozzle 28a has the self-recovery properties, the concave portion 78b of the air supply/water supply hole portion 78 receives reaction force from the convex portion 82c of the cover member 82. Therefore, it is possible to enhance an appressed state and a fixed state between the concave portion 78b and the outer peripheral surface 82a of the cover member 82. Therefore, when the concave portion 78b of the air supply/water supply hole portion 78 is pressed by using the annular convex portion 82c, the air-tightness and the water-tightness in the insertion portion 12 can be assured, and a state that a position of the nozzle 28a is set out with respect to the distal end hard portion 42 can be maintained.

Additionally, if the engaged state of the air supply/water supply hole portion 78 of the distal end cover 54 and the outer peripheral surface 82a of the cover member 82 of the nozzle 28a can be maintained while achieving the water-tightness and the air-tightness, the engagement between the distal end cover 54 and the outer peripheral surface 82a of the cover member 82 of the nozzle 28a can be modified in many ways. For example, it is also preferable to arrange, e.g., an O-ring between the air supply/water supply hole portion 78 and the outer peripheral surface 82a of the cover member 82 of the nozzle 28a and to thereby create the watertight and airtight state.

The endoscope according to this embodiment includes the distal end hard portion provided at the distal end portion of the insertion portion and the nozzle that is arranged to pass through the distal end hard portion and can emit a fluid. Further, the distal end hard portion includes: the cylindrical distal end main body having the first hole portion in which the nozzle is arranged; and the distal end cover which includes the second hole portion provided coaxially with the first hole portion and the first engagement portion provided at the edge portion of the second hole portion and covers the outer periphery of the distal end portion main body. Furthermore, the nozzle can elastically deform, has the self-restoration properties to hold its shape, and includes: the cylindrical cover member that includes the nozzle opening arranged at the position protruding with respect to the distal end surface of the distal end cover and the second engagement portion which is engaged with the first engagement portion of the distal end cover and configured to secure the air-tightness and the water-tightness in the insertion portion; the cylindrical coupling portion coupled with the first hole portion of the distal end portion main body; and the core member which has one end fixed to the cover member and the other end fixed to the coupling portion, is made of a material harder than the cover member and the coupling member, and has the flow path communicating with the nozzle opening.

According to this embodiment, when the nozzle is inserted into the first and second hole portions of the distal end hard portion, the coupling portion can be coupled with the first hole portion of the distal end portion main body, and a position of the nozzle can be set out with respect to the distal end hard portion by engaging the first and second engagement portions. The first and second engagement portions enable assuring the air-tightness and the water-tightness in the insertion portion. Further, since the cover member of the nozzle can elastically deform in accordance with its self-recovery properties, even if the cover member is pressed by a certain object, the cover member can maintain its shape, thereby maintaining the functions and the performance of the nozzle. Therefore, the self-restoration properties, i.e., the elastic force of the nozzle enables fixation to/removal from the distal end hard portion, whereby attachability/detachability at the time of attaching/detaching the nozzle to/from the distal end hard portion.

It is preferable that the first engagement portion of the distal end cover includes the annular protruding portion that presses the outer peripheral surface of the cover member toward the inner side of the cover member.

Since the cover member of the nozzle has the self-restoration properties, the annular protruding portion receives the reaction force from the outer peripheral surface of the cover member. Therefore, the appressed state and the fixed state of the protruding portion and the outer peripheral surface of the cover member can be enhanced. Therefore, when the outer peripheral surface of the cover member is pressed by using the annular protruding portion, the air-tightness and the water-tightness in the insertion portion can be assured, and a state that the nozzle is positioned with respect to the distal end hard portion can be maintained.

It is preferable that the second engagement portion of the cover member of the nozzle includes the annular concave groove that is pressed by the protruding portion.

When the cover member has the concave groove, the positional relationship between the concave groove and the protruding portion can be assuredly defined.

It is preferable that the first engagement portion of the distal end cover includes the annular concave portion in the second hole portion and the second engagement portion to have the annular convex portion engaged with the concave portion.

Since the cover member of the nozzle has the self-restoration properties, the second hole portion receives the reaction force from the protruding portion of the distal end cover. Therefore, the appressed state and the fixed state of the concave portion and the outer peripheral surface of the cover member can be enhanced. Therefore, when the annular concave portion of the second hole portion is pressed by using the annular convex portion, the air-tightness and the water-tightness in the insertion portion can be assured, and a state that the nozzle is positioned with respect to the distal end hard portion can be maintained.

It is preferable that the distal end portion main body includes the through hole communicating with the first hole portion and the core member includes on its outer peripheral surface the boss portion that engages with the through hole.

Using the boss portion enables regulating the axial movement and the circumferential movement of the nozzle with respect to the distal end hard portion.

It is preferable that the core member includes the annular concave portion on its outer peripheral surface, the coupling portion is arranged in the annular concave portion, and the one end of the coupling portion is away from the step of the annular concave portion.

When the one end of the coupling portion is away from the step of the annular concave portion, the coupling portion can be easily deformed without suppressing this deformation at a time of coupling (arranging) the coupling portion in the first hole portion of the distal end portion main body.

It is preferable that the core member includes on its outer peripheral surface the annular flange portion that abuts on the distal end surface of the distal end portion main body.

The annular flange can prevent the nozzle from moving toward the proximal end side. Therefore, the annular flange can be used for regulating the axial position of the nozzle (regulation of the axial position).

The endoscope according to this embodiment includes: the insertion portion including the distal end hard portion having the hole portion passing through the distal end surface; and the nozzle arranged in the hole portion of the distal end hard portion. The nozzle includes: the cylindrical cover member that can elastically deform, has the self-restoration properties to hold its shape, has the nozzle opening arranged at the position protruding with respect to the distal end surface of the distal end hard portion; the cylindrical coupling portion that can elastically deform, has the same self-restoration properties as the cover member, and is coupled with the distal end hard portion; and the cylindrical core member that is made of a material harder than the cover member and the coupling member, and has the flow path communicating with the nozzle opening, wherein the cover member is arranged on the one end of the cylindrical core member, and the coupling member is arranged on the other end of the cylindrical core member.

According to this embodiment, when the nozzle is inserted into the hole portion of the distal end hard portion, since the coupling portion has the self-restoration properties, the outer peripheral surface of the coupling portion can be coupled with the hole portion of the distal end hard portion in the appressed manner. Therefore, the nozzle can be positioned with respect to the distal end hard portion. Further, since the cover member of the nozzle can elastically deform in accordance with the self-restoration properties, the cover member can maintain its shape even after the cover member is pressed by a certain object, and hence the functions of the nozzle can be maintained. Therefore, the self-restoration properties, i.e., the elastic force of the nozzle enables fixation to/removal from the distal end hard portion, whereby attachability/detachability at the time of attaching/detaching the nozzle to/from the distal end hard portion.

It is preferable that at least one of the cover member, the core member, and the coupling portion includes the movement regulating portion that regulates the movement of the nozzle with respect to the distal end hard portion.

Therefore, it is possible to regulate the movement of the nozzle in, e.g., the axial direction or the circumferential direction with respect to the distal end hard portion.

It is preferable that the cover member and the coupling portion are made of the resin material, and the core member can fix the cover member and the coupling portion and is made of the metal material that is difficult to deform as compared with the cover member and the coupling portion.

Therefore, even if the cover member is pressed, the core member continuously maintains its shape, and hence the functions of the nozzle can be constantly maintained.

As described above, according to this embodiment, it is possible to provide the endoscope that can improve attachability/detachability for attaching/detaching the nozzle to/from the distal end portion of the insertion portion, namely, repairing properties of the nozzle without deteriorating the functions and the performance of the nozzle.

Second Embodiment

A second embodiment will now be described with reference to FIG. 10A to FIG. 17B. This embodiment is a modification of the first embodiment including the first and second modifications, like reference numerals denote members equal to those explained in the first embodiment, and a detailed description thereof will be omitted. It is to be noted that the description has been given as to the example where the nozzle 28a explained in the first embodiment is attached or detached by moving the nozzle 28a along the axial direction of the insertion portion 12. A description will be given as to an example where a nozzle 28a explained in this embodiment is attached or detached by moving the nozzle 28a along an axial direction of an insertion portion 12 and revolving the same about an axis of the insertion portion 12 (about a central axis C).

As shown in FIG. 10A to FIG. 12C, the nozzle 28a has a cylindrical core member (a base material) 202, an annular portion (a movement regulating portion; and an axial movement regulating portion) 204 having self-restoration properties, and a coupling portion (the movement regulating portion; the axial movement regulating portion; and the circumferential movement regulating portion) 206 having self-restoration properties.

The nozzle 28a is formed by, e.g., two-color molding, one end of the nozzle 28a on the outer side of the core member 202 is heat-sealed with respect to the annular portion 204, and the other end of the same is heat-sealed with respect to the coupling portion 206, thereby integrating these members. It is to be noted that the core member 202 is adjusted as a harder material than the annular portion 204 and the coupling portion 206, and the annular portion 204 and the coupling portion 206 have the same hardness when the nozzle 28a is formed based on the two-color molding. Moreover, the core member 202 must have hardness that allows insertion without buckling when the core member 202 is inserted into hole portions 68 and 78 of a distal end hard portion 42. Therefore, it is preferable for the core member 202 to be made of a metal material such as a stainless steel material. The hardness of each of the annular portion 204 and the coupling portion 206 is lower than a distal end portion main body 52 and a distal end cover 54 of the distal end hard portion 42.

Each of the annular portion 204 and the coupling portion 206 is formed of an elastic member that can be stretched in the radial direction and the axial direction when the nozzle 28a is attached to the distal end portion main body 52 and the distal end cover 54. Therefore, each of the annular portion 204 and the coupling portion 206 is made of a material that is flexible with respect to the distal end portion main body 52 and the distal end cover 54.

The cylindrical core member 202 includes a cylindrical body 212 having a defined central axis C and a nozzle head 214 which is formed integrally with the cylindrical body 214 and arranged at a position protruding with respect to a distal end surface 54a of the distal end cover 54.

The cylindrical body 212 has one end (a distal end) which locates the annular portion 204 on the outer side of the cylindrical body 212 and the other end (a proximal end) which locates the coupling portion 206 on the outer side of the cylindrical body 212. The nozzle head 214 is integrally formed at the one end of the cylindrical body 212 and includes a nozzle opening 214a. The core member 202 includes a flow path 202a through which a fluid can flow from the other end toward the one end of the cylindrical body 212 and which allows the fluid to be discharged from the nozzle opening 214a of the nozzle head 214.

The flow path 202a is bent, e.g., approximately 90° with respect to the central axis C of the cylindrical body 212 at one end of the cylindrical body 212, i.e., the nozzle head 214. Therefore, a liquid such as a normal saline solution or a gas such as air, i.e., a fluid is allowed to flow through the flow path 202a, this fluid can be ejected from the nozzle opening 214a toward an observation window 24a of an observation optical system 24.

The one end of the cylindrical body 212 and the nozzle head 214 are arranged to protrude with respect to a distal end surface 54a of the distal end cover 54 (the distal end surface 54a of the distal end hard portion 42). The coupling portion 206 is arranged to be appressed against an inner peripheral surface of a hole portion 68 of the distal end portion main body 52 and coupled with a distal end of an air supply/water supply pipe 28b.

The cylindrical body 212 has on its outer peripheral surface a large-diameter portion 222 engaged with the distal end cover 54 and a small-diameter portion 224 which has a smaller diameter than the large-diameter portion 222 and is arranged on the inner side of the air supply/water supply hole portion 68 of the distal end portion main body 52. A step 226 is formed between the large-diameter portion 222 and the small-diameter portion 224.

Figure 10A:
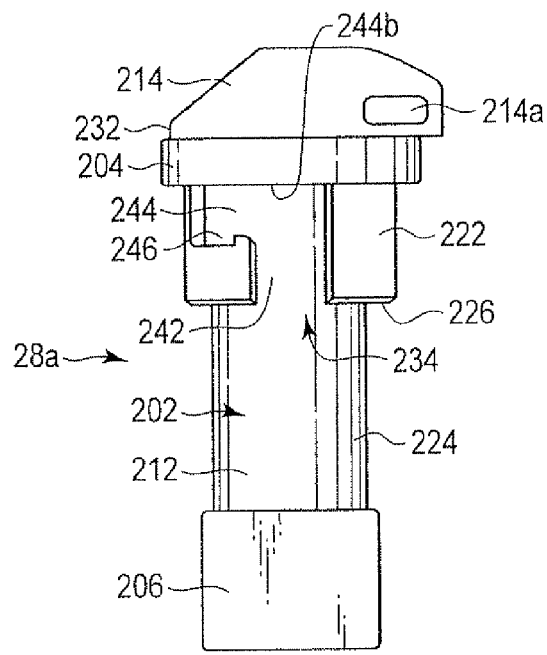
FIG. 10A is a schematic perspective view showing a nozzle attached to a distal end hard portion of an insertion portion of an endoscope according to a second embodiment.
Figure 10B:
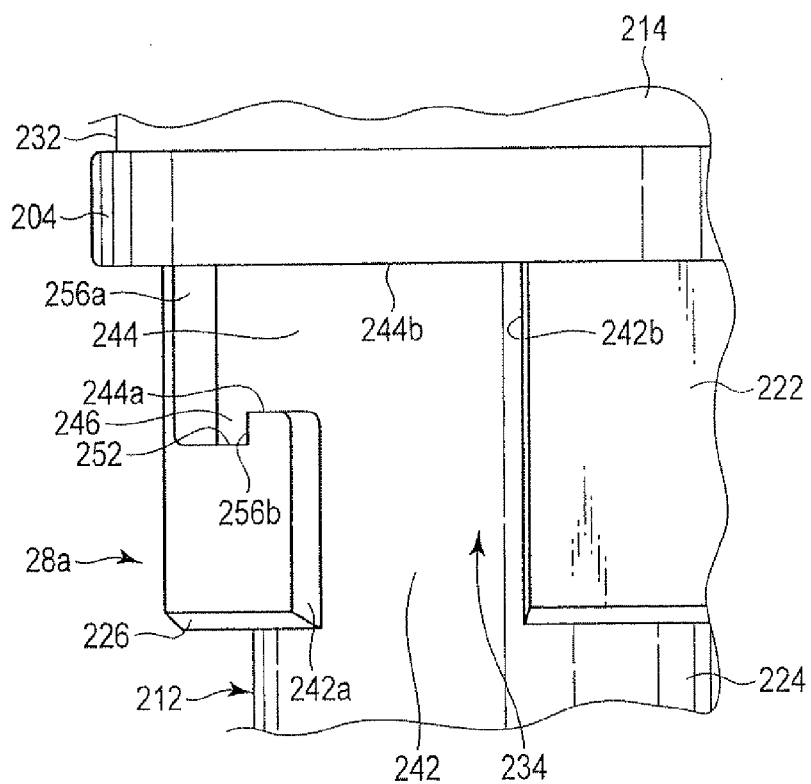
FIG. 10B is an enlarged schematic perspective view showing an engagement portion of a core member of the nozzle attached to the distal end hard portion of the insertion portion of the endoscope according to the second embodiment.

As shown in FIG. 10B, the large-diameter portion 222 includes a flange portion 232 which prevents the annular portion 204 from moving toward the nozzle head 214 side when the annular portion 204 is arranged and a groove portion 234 which is detachably engaged with the distal end cover 54. That is, the groove portion 234 of the cylindrical body 212 of the core member 202 forms an engagement portion (a second engagement portion). The flange portion 232 projects outward in the radial direction with respect to the central axis C of the cylindrical body 212, and it is appressed against an end surface of the annular portion 204 on a side close to the nozzle head 214. It is to be noted that the annular portion 204 is engaged with a later-described annular wall 262 of the hole portion 78 of the distal end cover 54, and it can be used as a sealing member (a second engagement portion) that prevents a liquid from entering the insertion portion 12 from the hole portion 78.

In the groove portion 234, a first axial groove (a first axial movable portion) 242 parallel to the axial direction (the central axis C) of the cylindrical body 212, a circumferential groove (a circumferential movable portion) 244 along the circumferential direction of the cylindrical body 212, and a second axial groove (a second axial movable portion) 246 parallel to the axial direction of the cylindrical body 212 are continuously formed. That is, the first and second axial grooves 242 and 246 are used as circumferential movement regulating portions, and the circumferential grove 244 is used as an axial movement regulating portion. It is to be noted that the first axial groove 242 and the second axial groove 246 are not only parallel to the central axis C but also sufficiently allowed to incline, e.g., approximately several degrees. Further, the circumferential groove 242 is not only orthogonal to the central axis C but also sufficiently allowed to incline, e.g., approximately several degrees.

The first axial groove 242 is formed between end surfaces 242a and 242b, which face each other, of the large-diameter portion 222. These end surfaces 242a and 242b allow movement in the axial direction and regulate movement in the circumferential direction when a later-described protruding portion 274 of the distal end cover 54 is arranged between the end surfaces 242a and 242b.

The circumferential groove 244 is formed between a lower end surface 244a of the large-diameter portion 222 provided away from the flange portion 232 or the annular portion 204 and an upper end surface 244b which faces this lower end surface 244a and is close to the flange portion 232 or the annular portion 204. These end surfaces 244a and 244b allow a later-described protruding portion 274 of the distal end cover 54 from moving in the circumferential direction and regulate the same from moving in the axial direction when the protruding portion 274 is arranged between the end surfaces 244a and 244b. It is to be noted that the lower end surface 244a functions as a projection that accommodates the later-described protruding portion 274 of the hole portion 78 of the distal end cover 54 in a later-described accommodating portion 252 of the second axial groove 246.

The second axial groove 246 includes an accommodating portion 252, in which the later-described protrusion portion 274 of the distal end cover 54 is accommodated, at a position facing the upper end surface 244b. Further, regulating surfaces 256a and 256b that regulate the circumferential movement of the later-described protruding portion 274 of the distal end cover 54 are formed at a portion of the large-diameter portion 222 that is orthogonal to the accommodating portion 252.

It is noted that the regulating surface 256a faces the regulating surface 256b and also faces the end surface 242b of the first axial groove 242. Furthermore, this end surface 242b functions as a regulating surface that regulates the movement of the later-described protruding portion 274 of the distal end cover 54.

A circumferential width of the first axial groove 242 of the groove portion 234 is substantially equal to a circumferential width of the accommodating portion 252 of the second axial groove 246, and these are formed to be slightly wider than a circumferential width of the later-described protruding portion 274 of the distal end cover 54. Moreover, an axial width of between the end surfaces 244a and 244b of the circumferential groove 244 is formed to be slightly larger than a thickness of the protruding portion 274 of the distal end cover 54.

Figure 11A:
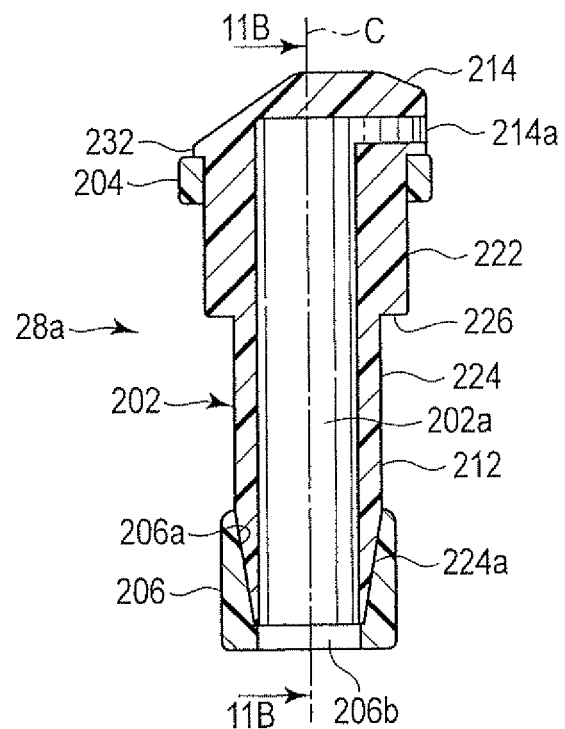
FIG. 11A is a cross-sectional view taken along a line 11A-11A in FIG. 11B, showing the nozzle attached to the distal end hard portion of the insertion portion of the endoscope according to the second embodiment.
Figure 11B:
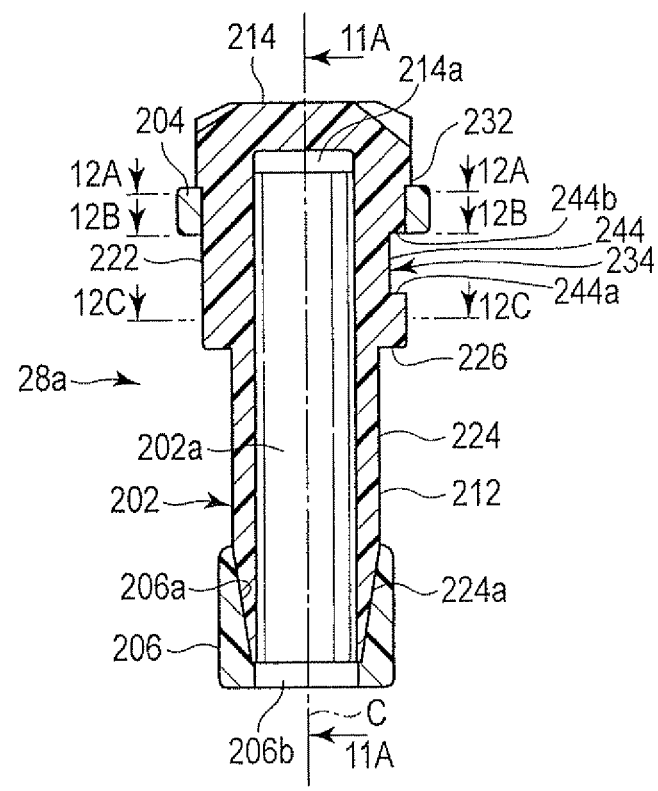
FIG. 11B is a cross-sectional view taken along a line 11B-11B in FIG. 11A, showing the nozzle attached to the distal end hard portion of the insertion portion of the endoscope according to the second embodiment.
Figure 12A:
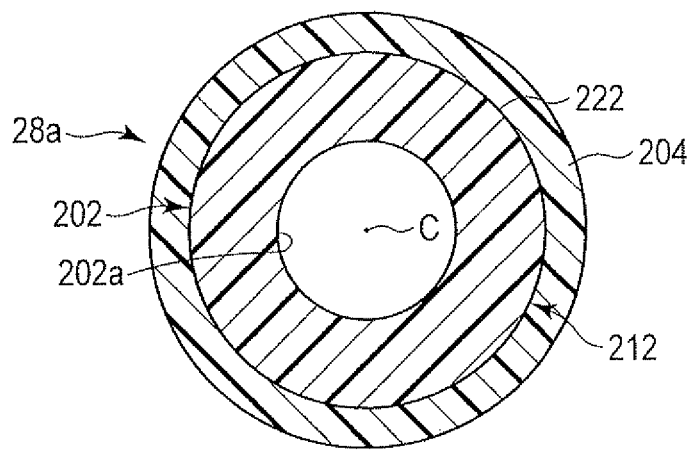
FIG. 12A is a cross-sectional view taken along a line 12A-12A in FIG. 11B, showing the nozzle attached to the distal end hard portion of the insertion portion of the endoscope according to the second embodiment.
Figure 12B:
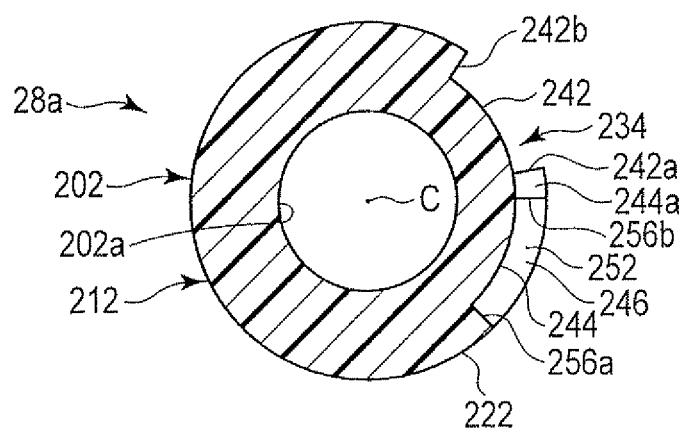
FIG. 12B is a cross-sectional view taken along a line 12B-12B in FIG. 11B, showing the nozzle attached to the distal end hard portion of the insertion portion of the endoscope according to the second embodiment.
Figure 12C:
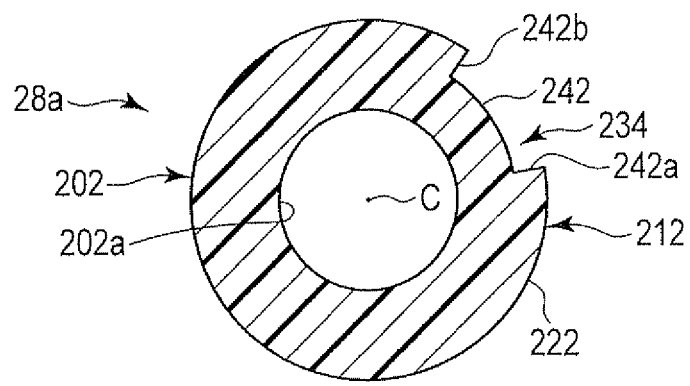
FIG. 12C is a cross-sectional view taken along a line 12C-12C in FIG. 11B, showing the nozzle attached to the distal end hard portion of the insertion portion of the endoscope according to the second embodiment.

As shown in FIG. 11B and FIG. 12A, in the large-diameter portion 222 of the cylindrical body 212, a transverse cross section of an outer peripheral surface at a position where the annular portion 204 is arranged is formed into a circular shape. As shown in FIG. 11B and FIG. 12B, in the cylindrical body 212, an outer peripheral surface at a position where the groove portion 234 is formed is partially notched by the first axial groove 242, the circumferential groove 244, and the second axial groove 246. As shown in FIG. 11B and FIG. 12C, in the core member 202, an outer peripheral surface at a position where the groove portion 234 is formed is partially notched by the first axial groove 242.

As shown in FIG. 11A and FIG. 11B, in the small-diameter portion 224 of the cylindrical body 212, a taper portion (an inclined portion) 224a whose diameter is reduced as getting closer to the proximal end side is formed on an outer peripheral surface at the other end of the cylindrical body 212. On the other hand, on an inner peripheral surface of the coupling portion 206, a taper portion (an inclined portion) 206a that is fixed to the taper portion 224a of the small-diameter portion 224 of the cylindrical body 212 is formed. The taper portion 206a has the same taper angle as the taper portion 224a of the small-diameter portion 224 of the cylindrical body 212, and it is formed in such a manner that its diameter is reduced as getting closer to the proximal end side. Therefore, a contact area of the taper portion 224a of the small-diameter portion 224 of the cylindrical body 212 and the taper portion 206a on the inner peripheral surface of the coupling portion 206 can be increased beyond that in a case where the taper portions 224a and 206a are not formed. Therefore, fixing force that fixes the coupling portion 206 to the cylindrical body 212 can be increased.

It is to be noted that the coupling portion 206 is formed to be continuous with respect to the taper portion 206a and includes a flow path 206b communicating with the flow path 202a of the core member 202. Here, it is preferable that an outside diameter of the coupling portion 206 is the same from the proximal end to the distal end or is larger on the proximal end than on the distal end. Therefore, a thickness of the coupling portion 206 in the radial direction is increased as getting closer to the proximal end side. Therefore, in the coupling portion 206, since a wall thickness in the radial direction becomes larger as getting closer to the proximal end side, the proximal end of the coupling portion 206 can be readily elastically deformed.

Further, a maximum outside diameter of the coupling portion 206 when the coupling portion 206 is not elastically deformed is equal to or slightly smaller than an inside diameter of the small-diameter portion 69b (see FIG. 16A and FIG. 16B) of the air supply/water supply hole portion 68 of the distal end portion main body 52. The flow path 206b of the coupling portion 206 is pressed toward the distal end side when the distal end of the air supply/water supply pipe 28b is allowed to abut on the proximal end of the coupling portion 206, and the proximal end of the coupling portion 206 elastically deforms inward in the radial direction and outward in the radial direction. At this time, the outer peripheral surface of the coupling portion 206 that elastically deforms outward in the radial direction is appressed against the small-diameter hole 69b of the hole portion 68 of the distal end portion main body 52. Therefore, the coupling portion 206 can communicate with the air supply/water supply pipe 28b while maintaining water-tightness between itself and the small-diameter hole 69b of the hole portion 68.

It is to be noted that the maximum outside diameter of the coupling portion 206 when the coupling portion 206 is not elastically deformed is formed to be larger than the maximum outside diameter of the small-diameter portion 224 of the cylindrical body 212 and smaller than the maximum outside diameter of the large-diameter portion 222.

Figure 13A:
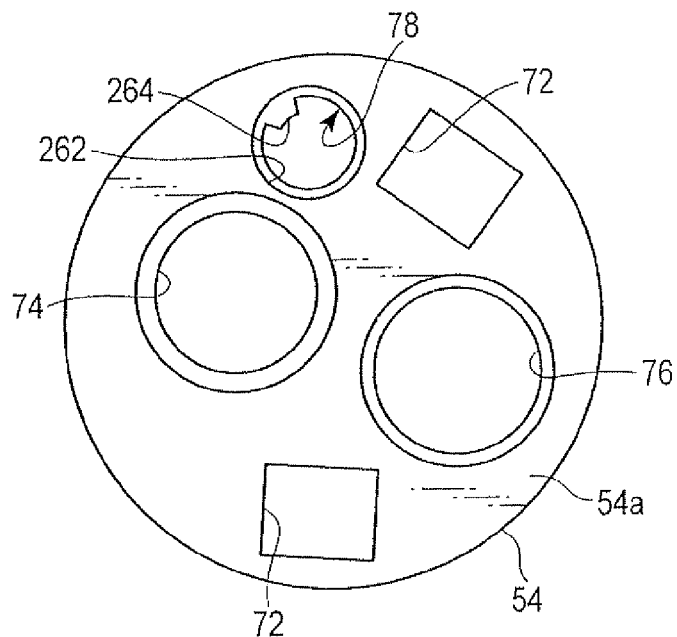
FIG. 13A is a schematic front view showing a distal end cover arranged at the distal end hard portion of the insertion portion of the endoscope according to the second embodiment.

As shown in FIG. 13A, like the first embodiment mentioned above, the distal end cover 54 according to this embodiment includes an illumination optical system hole portion 72, an observation optical system hole portion 74, a channel hole portion 76, and an air supply/water supply hole portion 78 in which the nozzle 28a is arranged. Of these members, the air supply/water supply hole portion 78 includes: an annular wall 262 having an outside diameter greatly smaller than an outside diameter of the annular portion 204; an engagement portion (a first engagement portion) 264 engaged with an engagement portion (the second engagement portion) cooperated with the annular portion 204 and the groove portion 234 of the large-diameter portion 222.

It is preferable that the annular wall 262 is formed as a surface orthogonal to the distal end surface 54a of the distal end cover 54. It is preferable that a height of this annular wall 206 is substantially equal to a thickness of the annular portion 204. Since the outside diameter of the annular portion 204 is slightly larger than the outside diameter of the annular wall 262, the liquid can be prevented from entering the inside of the insertion portion 12 from the hole portion 78 when the annular portion 204 is arranged on the annular wall 262.

The engagement portion 264 is provided at the edge portion of the hole portion 78. The engagement portion 264 includes a mounting portion 272 on which the upper end surface 244b of the large-diameter portion 222 of the core member 202 is mounted in a contact manner at the time of attaching or detaching the nozzle 28a, a protruding portion 274 which is formed as a part of the mounting portion 272 and projects inward along the radial direction, and end portions 276a and 276b formed at side end portions of the protruding portion 274 in the circumferential direction, respectively. The protruding portion 274 has a circumferential width that is slightly smaller than the circumferential width of each of the first and second axial grooves 242 and 246 of the large-diameter portion 222 of the cylindrical body 212 of the nozzle 28a. In addition, it is preferable that the mounting portion 272 is formed as a surface parallel to the distal end surface 54a of the distal end cover 54.

The mounting portion 272 and the protruding portion 274 of the air supply/water supply hole portion 78 of the distal end cover 54 are formed in such a manner that the coupling portion 206 of the nozzle 28a can be inserted from a front surface side (the distal end surface 54a) toward a back surface side thereof and the large-diameter portion 222 of the cylindrical body 212 cannot be inserted from the front surface side (the distal end surface 54a) side toward the back surface side at positions other than the first axial groove 242. That is, a protruding length of the protruding portion 274 from the mounting portion 272 is set in this manner. It is to be noted that a thickness of the protruding portion 274 can be appropriately set, but it is preferably set to be smaller than a width between the end surfaces 244a and 244b of the circumferential groove 244 and larger than a height of a protrusion (the end surface) 244a from the accommodating portion 252 shown in FIG. 10B.

Figure 16A:
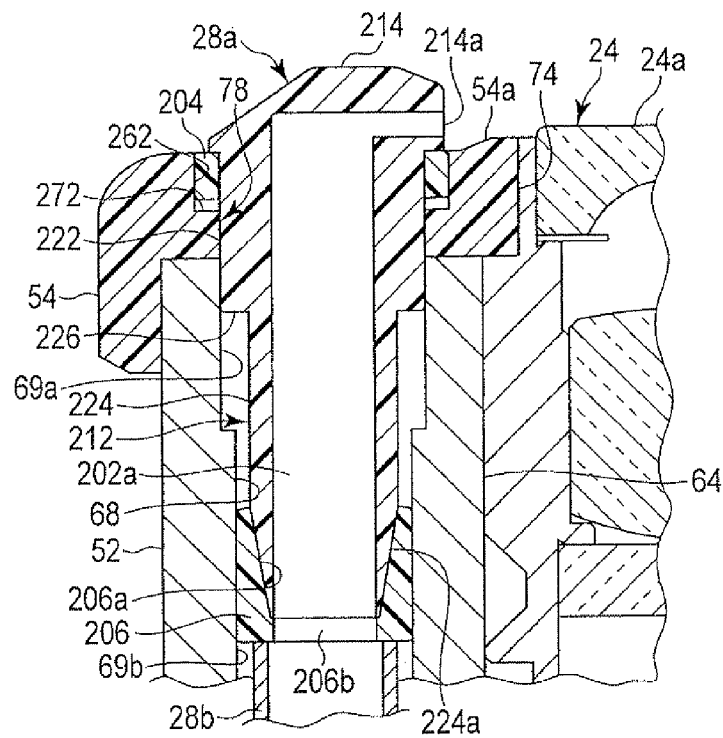
FIG. 16A is a cross-sectional view taken along a line 16A-16A in FIG. 15, showing a state that the nozzle is attached to the distal end hard portion of the insertion portion of the endoscope according to the second embodiment.
Figure 16B:
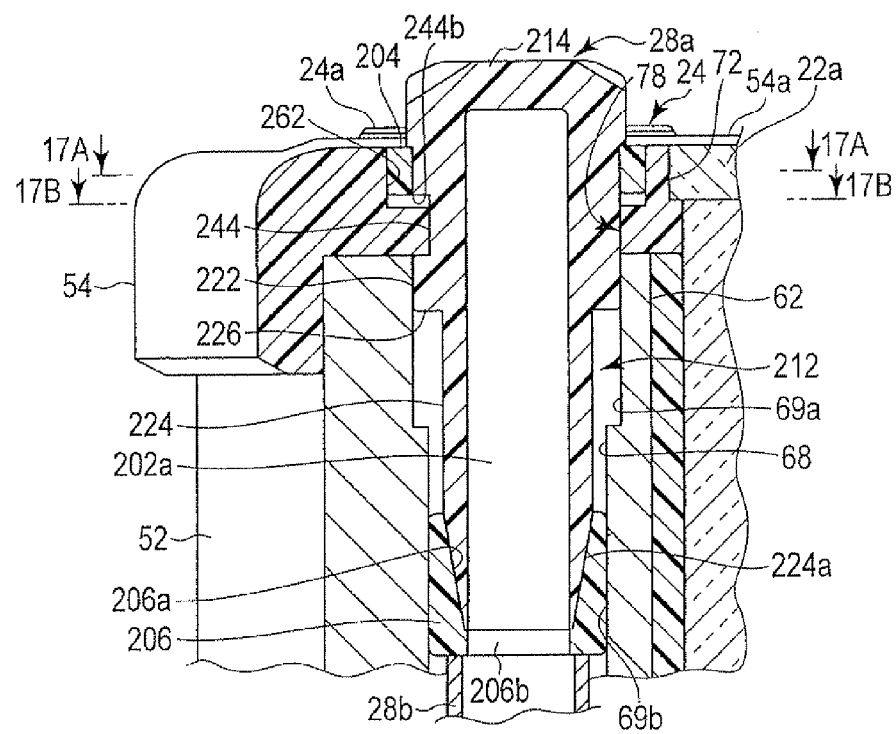
FIG. 16B is a cross-sectional view taken along a line 16B-16B in FIG. 15, showing a state that the nozzle is attached to the distal end hard portion of the insertion portion of the endoscope according to the second embodiment.
Figure 17A:
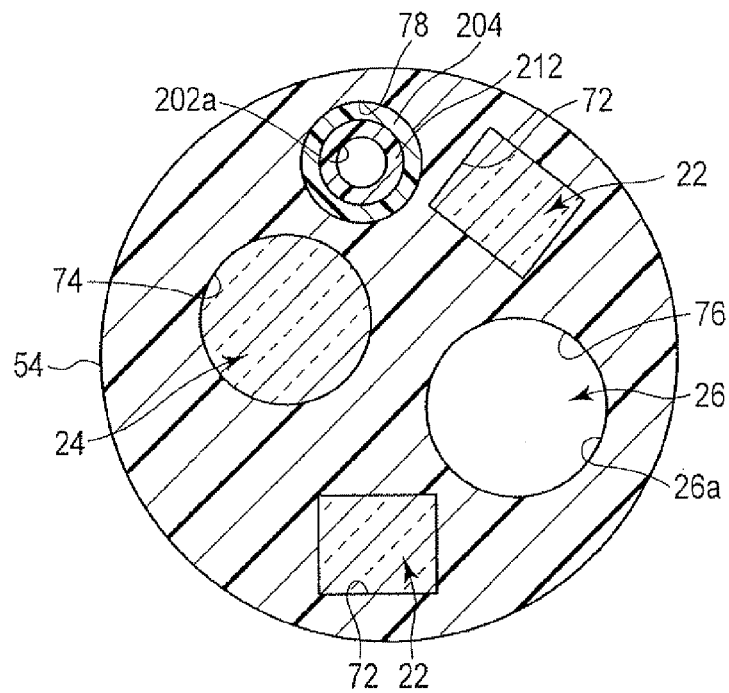
FIG. 17A is a cross-sectional view taken along a line 17A-17A in FIG. 16B, showing a state that the nozzle is attached to the distal end hard portion of the insertion portion of the endoscope according to the second embodiment.
Figure 17B:
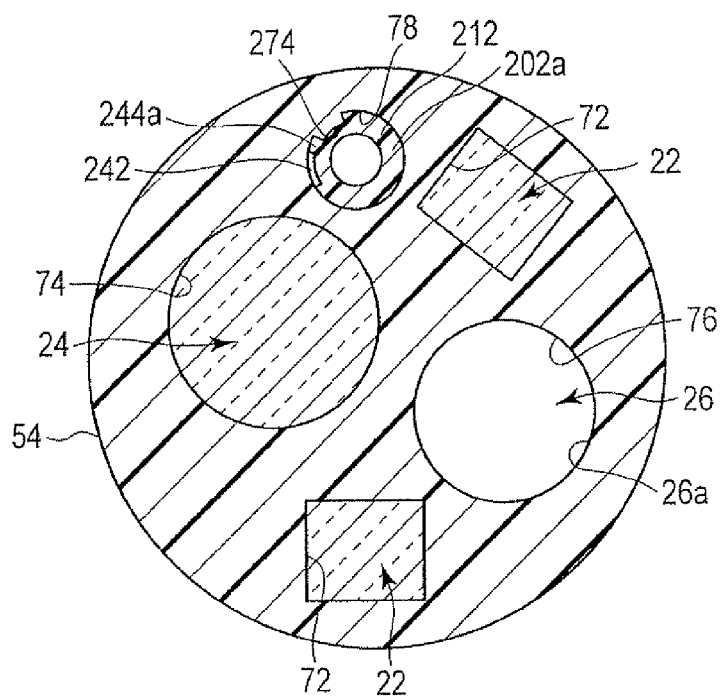
FIG. 17B is a cross-sectional view taken along a line 17B-17B in FIG. 16B, showing a state that the nozzle is attached to the distal end hard portion of the insertion portion of the endoscope according to the second embodiment.

As shown in FIG. 16A and FIG. 16B, the distal end portion main body 52 includes an illumination optical system hole portion 62 in which an illumination optical system 22 is arranged, an observation optical system hole portion 64 in which an observation optical system 24 is arranged, a channel hole portion (not shown), and the air supply/water supply hole portion (a first hole portion) 68 in which the air supply/water supply nozzle 28a is arranged. The air supply/water supply hole portion 68 includes a large-diameter hole 69a in which the large-diameter portion 222 of the cylindrical body 212 of the nozzle 28a is arranged and a small-diameter hole 69b in which the coupling portion 206 is arranged. The large-diameter hole 69a is formed to be slightly larger than the large-diameter portion 222 of the cylindrical body 212. The small-diameter hole 69b is formed to be equal to or slightly smaller than the coupling portion 206. It is to be noted that the air supply/water supply pipe 28b is fixed to or integrally formed with the distal end portion main body 52 as described in the first embodiment.

Functions of the endoscope 10 according to this embodiment will now be described. Here, a description will be given as to an example where the air supply/water supply nozzle 28a is attached to the distal end hard portion 42 of the insertion portion 12 of the endoscope 10.

Figure 14:
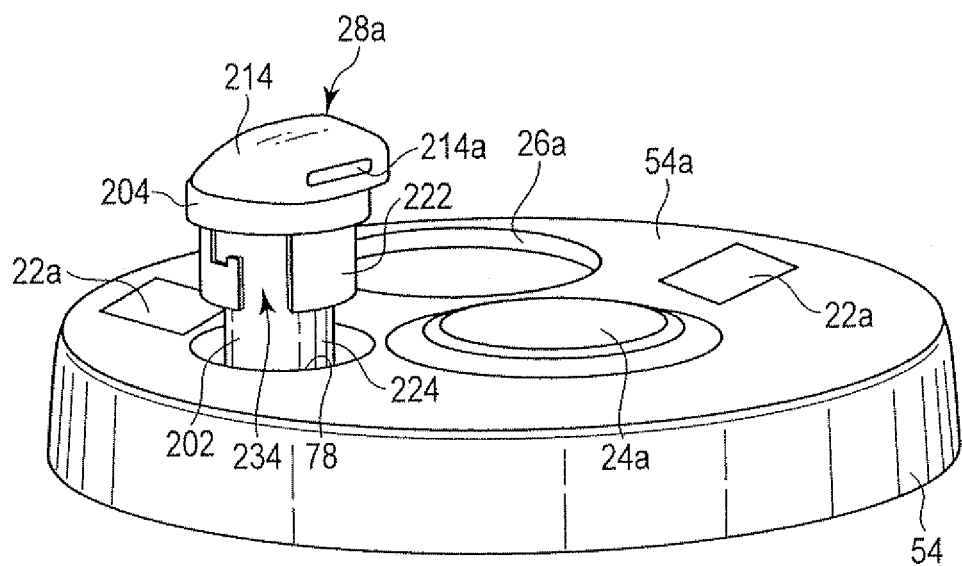
FIG. 14 is a schematic perspective view showing a state that the nozzle is to be inserted into the air supply/water supply hole portion in the distal end cover at the distal end hard portion of the insertion portion of the endoscope according to the second embodiment.

As shown in FIG. 14, the nozzle opening 214a of the nozzle head 214 is arranged to face the outside of the distal end cover 54. That is, the nozzle opening 214 is set to not face the illumination window 22a or the observation window 24a. In this state, the coupling portion 206 of the nozzle 28a is inserted into the air supply/water supply hole portion 78 of the distal end cover 54 and the air supply/water supply hole portion 68 of the distal end portion main body 52 in the mentioned order along the central axis C of the cylindrical body 212. At this time, although the protruding portion 274 is present in the hole portion 78 of the distal end cover 54, the coupling portion 206 can be inserted. Therefore, the coupling portion 206 of the nozzle 28a is inserted into the hole portion 68 of the distal end portion main body 52.

When the step 226 of the cylindrical body 212 of the core member 202 of the nozzle 28a is mounted on the protruding portion 274 formed in the hole portion 78 of the distal end cover 54, the nozzle 28a is caught by the hole portion 78 of the distal end cover 54, and the nozzle 28a cannot be inserted deeply along the central axis C. At this time, the cylindrical body 212 of the nozzle 28a is revolved about its central axis C. The first axial groove 242 of the large-diameter portion 222 of the cylindrical body 212 of the nozzle 28a is arranged to face the protruding portion 274 of the engagement portion 264 of the air supply/water supply hole portion 78. The first axial groove 242 is moved with respect to the protruding portion 274, and the nozzle 28a is deeply pushed in.

Here, as shown in FIG. 16A and FIG. 16B, the proximal end of the coupling portion 206 of the nozzle 28a is mounted on the distal end of the air supply/water supply pipe 28b on the inner side of the small-diameter portion 69b of the air supply/water supply hole portion 68. At this time, the upper end surface 244b of the large-diameter portion 222 of the core member 202 faces the mounting portion 272 and the protruding portion 274 by elastic force of the coupling portion 206, but it is away from the upper end surface 244b of the large-diameter portion 222 of the core member 202, the mounting portion 272, and the protruding portion 274. Further, the protruding portion 274 is arranged between the end portions 242a and 242b of the first axial groove 242 of the large-diameter portion 222 of the core member 202.

Figure 15:
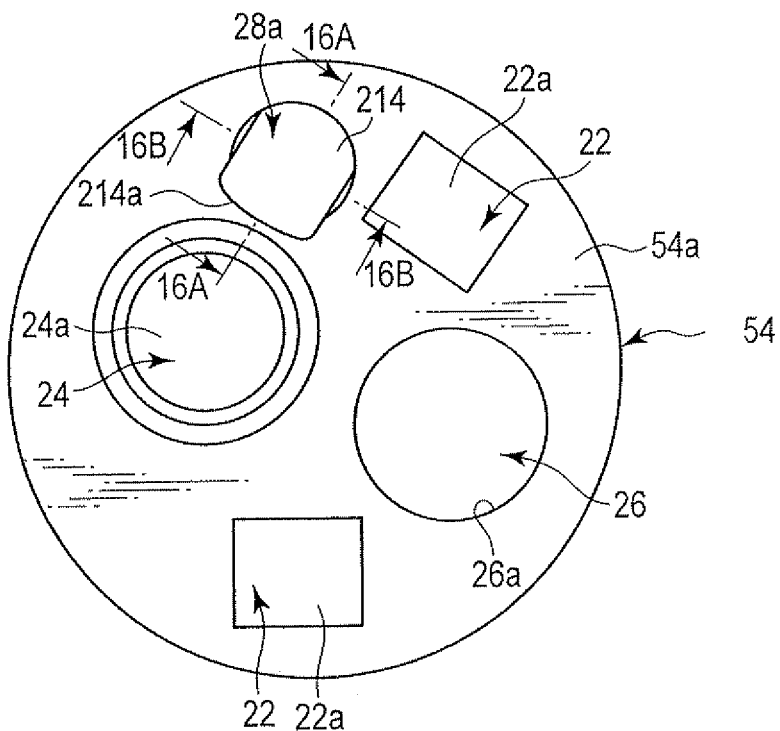
FIG. 15 is a schematic front view showing the distal end hard portion of the insertion portion of the endoscope according to the second embodiment.

In this state, the cylindrical body 212 is pushed into the hole portion 78 of the distal end cover 54 and the hole portion 68 of the distal end portion main body 52 along the central axis C and then rotated about its central axis C, namely, the nozzle opening 214a of the nozzle head 214 is rotated toward the observation window 24a to shift from the state shown in FIG. 14 to the state shown in FIG. 15.

In case of pushing the cylindrical body 212 into the hole portion 78 of the distal end cover 54 and the hole portion 68 of the distal end portion main body 52, the cylindrical body 212 is pushed in against the elastic force of the coupling portion 206 and also pushed in so that the annular portion 204 is arranged on the inner side of the annular wall 262 against the elastic force of the annular portion 204.

At this time, the surfaces of the mounting portion 272 and the protruding portion 274 of the engagement portion 264 of the hole portion 78 of the distal end cover 54 abut on the upper end surface 244b of the nozzle 28a. Furthermore, in a state that the upper end surface 244b of the nozzle 28a abuts on the surfaces of the mounting portion 272 and the protruding portion 274 of the engagement portion 264 of the hole portion 78 of the distal end cover, the cylindrical body 212 of the nozzle 28a is turned around its central axis C. Here, the protruding portion 274 of the engagement portion 264 of the hole portion 78 of the distal end cover 54 is relatively moved toward the second axial groove 246 from the first axial groove 242 of the nozzle 28a via the portion between the end surfaces 244a and 244b of the circumferential groove 244 against frictional force between the outer peripheral surface of the annular portion 204 of the nozzle 28a and the annular wall 262 of the distal end cover 54.

Here, a circumferential width of the accommodating portion 252 continuous with the regulating surfaces 256a and 256b of the second axial groove is larger than a circumferential width of the protruding portion 274 of the hole portion 78 of the distal end cover 54. Therefore, when the cylindrical body 212 is rotated around its central axis C, the regulating surface 256a of the large-diameter portion 222 of the nozzle 28a abuts on the one end portion 276b of the protruding portion 274 of the hole portion 78 of the distal end cover 54. Additionally, the elastically deformed coupling portion 206 exercises restoring force to recover to an original state. Therefore, the nozzle head 214 of the nozzle 28a moves to relatively project from the distal end surface 54a of the distal end cover 54 of the distal end hard portion 42 by the elastic force of the coupling portion 206, and the protruding portion 274 of the hole portion 78 is accommodated in the accommodating portion 252 of the nozzle 28a. At this time, a back side of the protruding portion 274 of the hole portion 78 of the distal end cover 54 changes from a position where it is contact with the protrusion 244a of the nozzle 28a to a position where it is accommodated in the accommodating portion 252. Therefore, a position of the nozzle 28a with respect to the distal end cover 54 moves upward (the side where the nozzle 28a protrudes from the distal end surface 54a of the distal end cover 54) a distance corresponding to the height of the projection 244a.

At this time, the movement of the nozzle 28a in the axial direction with respect to the hole portion 78 of the distal end cover 54 is prevented by pressing the back side of the protruding portion 274 of the hole portion 78 using the accommodating portion 252 of the nozzle 28a with use of the elastic force of the coupling portion 206 of the nozzle 28a. The movement of the nozzle 28a in the circumferential direction with respect to the hole portion 78 of the distal end cover 54 is prevented by sandwiching the end portions 276a and 276b of the protruding portion 274 of the hole portion 78 between the regulating surfaces 256a and 256b of the nozzle 28a. Therefore, the nozzle 28a is held with respect to the hole portion 78a of the distal end cover 54 by regulating disengagement of these members. That is, the large-diameter portion 222 of the nozzle 28a is engaged with the distal end cover 54.

It is to be noted that, since the outer peripheral surface of the annular portion 204 can be appressed against the inner peripheral surface (the annular wall 262) of the air supply/water supply hole portion 78, the water-tightness and the air-tightness between the outer peripheral surface of the annular portion 204 and the air supply/water supply hole portion 78 of the distal end cover 54 can be assured.

When the nozzle 28a is fitted to the distal end cover 54 in this manner, as shown in FIG. 16A and FIG. 16B, the proximal end of the coupling portion 206 of the nozzle 28a abuts on the distal end of the air supply/water supply pipe 28b on the inner side of the small-diameter portion 69b of the air supply/water supply hole portion 68. Here, the proximal end of the coupling portion 206 is formed to be thicker in the radial direction than the distal end of the same by the taper portion 206a. Therefore, when the distal end of the air supply/water supply pipe 28b is appressed against the proximal end of the coupling portion 206, the distal end of the pipe 28b exercises force to push away the proximal end of the coupling portion 206, and hence the proximal end of the coupling portion 206 can be elastically deformed outward in the radial direction. Therefore, the proximal end of the coupling portion 206 can be appressed against the inner peripheral surface of the small-diameter portion 69b of the air supply/water supply hole portion 68, and the water-tightness and the air-tightness between the outer peripheral surface of the coupling portion 206 and the air supply/water supply hole portion 68 of the distal end portion main body 52 can be assured.

When the proximal end of the coupling portion 206 is appressed against the inner peripheral surface of the small-diameter portion 69b of the air supply/water supply hole portion 68 in this manner, the movement of the nozzle 28a in the axial direction can be regulated, and the movement of the same in the circumferential direction can be also regulated. The coupling portion 206 allows the nozzle 28a to move in a predetermined range along the axial direction with respect to the distal end portion main body 52, i.e., the distal end hard portion 42, and it can support the nozzle 28a with respect to the distal end main body 52, i.e., the distal end hard portion 42. Further, the coupling portion 206 allows the nozzle 28a to move in a predetermined range along the circumferential direction with respect to the distal end portion main body 52, i.e., the distal end hard portion 42, and it can lock the nozzle 28a with respect to the distal end portion main body 52, i.e., the distal end hard portion 42.

That is, the nozzle 28a can be moved along the axial direction (the central axis C) of the core member 202 with respect to the distal end hard portion 42 by using the members denoted by, e.g., reference signs 242, 244b, 272, and 274, the core member 202 can be supported at a predetermined position with respect to the distal end cover 54, the core member 202 can be moved in a predetermined range along the circumferential direction with respect to the distal end cover 54 by using the members denoted by, e.g., reference signs 244, 272, and 274, and the core member 202 can be locked at a predetermined position with respect to the distal end cover 54 by using the members denoted by, e.g., reference signs 244a, 252, 256b, and 274.

Therefore, the groove portion 234 forms an axial support portion which allows the movement of the core member 202 in the predetermined range in the axial direction with respect to the distal end cover 54 by using the first and second axial grooves 242 and 246 of the groove portion 234, supports the end surface 244b of the circumferential groove 244 of the large-diameter portion 222 on the mounting portion 272 of the distal end cover 54, and supports the core member 202 with respect to the distal end cover 54. Furthermore, the accommodating portion 252 of the nozzle 28a and the protruding portion 274 of the hole portion 78 of the distal end cover 54 form a locking portion which allows the movement of the core member 202 in the predetermined range along the circumferential direction with respect to the distal end cover 54 and locks the core member 202 with respect to the distal end cover 54.

A situation that the nozzle 28a described in this embodiment is removed from the distal end hard portion 42 will now be briefly explained.

The nozzle 28a having the nozzle opening 214a facing the observation window 24a is pushed in toward the inner side of the hole portions 68 and 78 of the distal end hard portion 42 along the central axis C of the core member 202 of the nozzle 28a. Since the proximal end of the coupling portion 206 abuts on the distal end of the air supply/water supply pipe 28b, the proximal end side of the coupling portion 206 is elastically deformed with respect to the distal end of the air supply/water supply pipe 28b in particular, and further large reaction force is generated with respect to a state that the distal end hard portion 42 includes the nozzle 28a attached thereto. Moreover, since the outer peripheral surface of the annular portion 204 of the nozzle 28a is also appressed against the annular wall 262 of the hole portion 78 of the distal end cover 54, this outer peripheral surface is elastically deformed, and reaction force is produced.

At this time, the accommodating portion 252 of the nozzle 28a moves away from the back side of the protruding portion 274 of the hole portion 78 of the distal end cover 54. Therefore, the protruding portion 274 of the hole portion 78 of the distal end cover 54 is arranged in the circumferential groove 244 of the large-diameter portion 222. In this state, the nozzle opening 214a of the nozzle 28a is turned to face the outer side of the distal end cover 54. At this time, the protruding portion 274 of the hole portion 78 of the distal end cover 54 is relatively moved along a portion between the end surfaces 244a and 244b of the circumferential groove 244 of the nozzle 28a so that the end portion 276a of the protruding portion 274 is brought into contact with the end surface 242b of the axial groove 242. At this time, the protruding portion 274 is arranged in the first axial groove 242.

Since the protruding portion 274 of the hole portion 78 of the distal end cover 54 can relatively move along the first axial groove 244 between the end surfaces 242a and 242b of the large-diameter portion 222, the nozzle head 214 of the nozzle 28a further protrudes from the distal end surface 54a of the distal end cover 54 by the elastic force (the self-restoration force) of the coupling portion 206. Additionally, since the proximal end of the coupling portion 206 abuts on the distal end of the air supply/water supply pipe 28b, when the large-diameter portion 222 of the nozzle 28a is disengaged from the distal end cover 54, the coupling portion 206 produces the reaction force with respect to the distal end of the air supply/water supply pipe 28b, and the coupling portion 206 contracts inward along the radial direction. Therefore, the appressed state of the distal end portion main body 52 with respect to the inner peripheral surface of the air supply/water supply hole portion 68 is released, and the nozzle head 214 of the nozzle 28a further projects from the distal end surface 54a of the distal end cover 54 by the elastic force of the coupling portion 206.

In this state, the nozzle 28a is pulled out from the distal end hared portion 42. It is to be noted that, when the outer peripheral surface of the annular portion 204 of the nozzle 28a is appressed against the annular wall 262 of the hole portion 78 of the distal end cover 54, the nozzle 28a is pulled out against adhesion force between these members.

In this manner, the nozzle 28a can be attached to/detached from the distal end hard portion 42.

As described above, according to this embodiment, the following matters can be said.

The large-diameter portion 222 of the nozzle 28a can be engaged with and attached to the distal end cover 54 of the distal end hard portion 42 by just combining the movement in the axial direction, the movement in the circumferential direction, and the further movement in the axial direction. Therefore, the nozzle 28a can be readily fitted to or removed from the distal end hard portion 42.

To assure the water-tightness, the nozzle 28a according to this embodiment does not have to be fixed to the distal end hard portion 42 by using a sealing material or the like. Therefore, a large effect can be exercised with respect to repairing properties of the nozzle 28a.

It is to be noted that, in this embodiment, the description has been given as to the example where one protruding portion (the engagement portion) 274 of the hole portion 78 in the distal end cover 54 is engaged with one groove portion (the engagement portion) 234 of the nozzle 28a, but the two or more protruding portions may be engaged with two or more groove portions. That is, providing the multiple engagement portions with respect to the other multiple engagement portions is preferable as a matter of course.

Figure 13B:
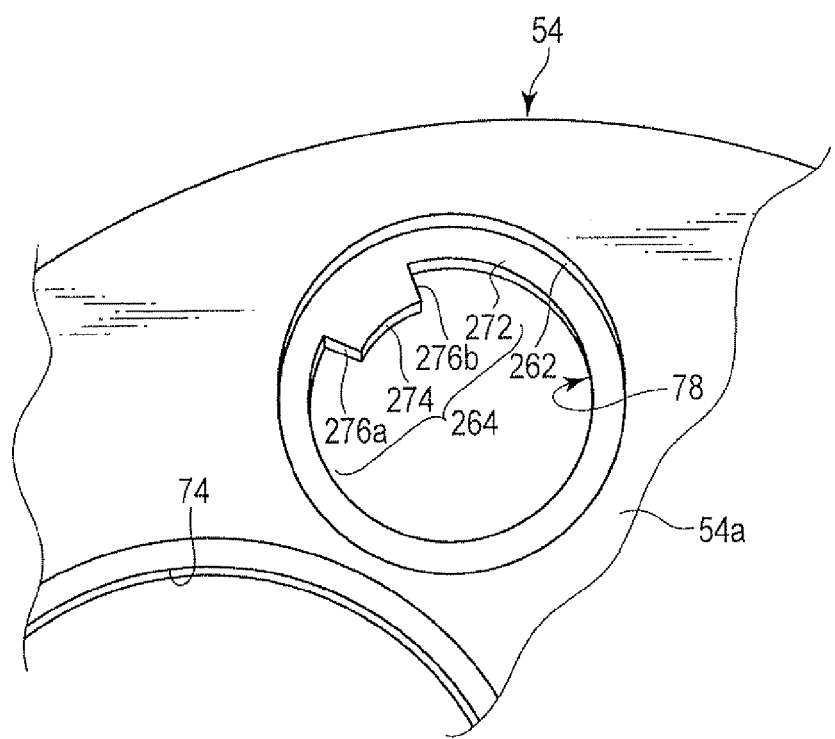
FIG. 13B is an enlarged schematic perspective view showing an air supply/water supply hole portion in the distal end cover at the distal end hard portion of the insertion portion of the endoscope according to the second embodiment.

Further, in this embodiment, although the description has been given as to the example where the annular wall 262 in FIG. 13B is formed as a surface parallel to the axial direction, forming the annular wall 262 like the annular projection portion 78a shown in FIG. 4 is also preferable. Furthermore, not only the annular portion 204 has the outer peripheral surface shown in FIG. 10B, but also the annular portion 204 can be preferably formed like the annular convex portion 82c shown in FIG. 7A to FIG. 7E.

Furthermore, it is also preferable that the structure of the air supply/water supply hole portion 68 of the distal end portion main body 52 and the structure of the coupling portion 206 of the nozzle 28a according to the second embodiment are formed like the structure of the air supply/water supply hole portion 68 of the distal end portion main body 52 and the structure of the coupling portion 86 of the nozzle 28a according to the first embodiment, respectively. Contrarily, it is also preferable that the structure of the air supply/water supply hole portion 68 of the distal end portion main body 52 and the structure of the coupling portion 86 of the nozzle 28a according to the first embodiment are formed like the structure of the air supply/water supply hole portion 68 of the distal end portion main body 52 and the structure of the coupling portion 206 of the nozzle 28a according to the second embodiment, respectively.

It is to be noted that, in FIG. 11B, the end surface of the annular portion 204 isolated from the flange portion 232 is shown as if it is level with the upper end surface 244b, but providing the end surface of the annular portion 204 isolated from the flange portion 232 on the side close to the flange portion 232 rather than the upper end surface 244b is also preferable.

[First Modification]

A first modification of the second embodiment will now be described with reference to FIG. 18A to FIG. 19B. In this modification, like reference numerals denote members equal to those explained in the first embodiment and the second embodiment including the respective modifications, and a detailed description thereof will be omitted.

In this modification, an example using an annular portion (a movement regulating portion; and an axial movement regulating portion) 204a obtained by modifying the annular portion 204 shown in FIG. 11A and FIG. 11B will be described. Here, a description will be given as to an example where the nozzle 28a is attached to the distal end hard portion 42 and the protruding portion 274 is pressed by a later-described upper end surface 244c of the annular portion 204a in this state so that the protruding portion 274 can be accommodated in the accommodating portion 252.

It is to be noted that the annular portion 204a can be used as an engagement portion (a second engagement portion) engaged with the hole portion 78 of the distal end cover 54 and also used as a sealing member that prevents a liquid from entering the insertion portion 12 from the hole portion 78.

Figure 18A:
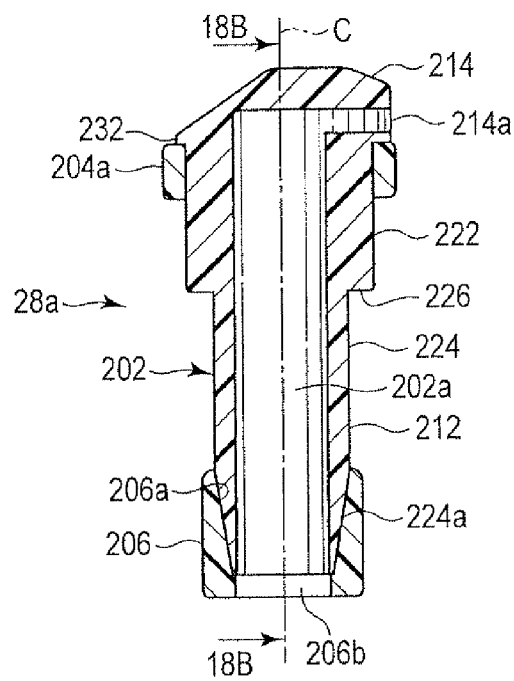
FIG. 18A is a cross-sectional view taken along a line 18A-18A in FIG. 18B, showing a state that a nozzle is attached to a distal end hard portion of an insertion portion of an endoscope according to a first modification of the second embodiment.
Figure 18B:
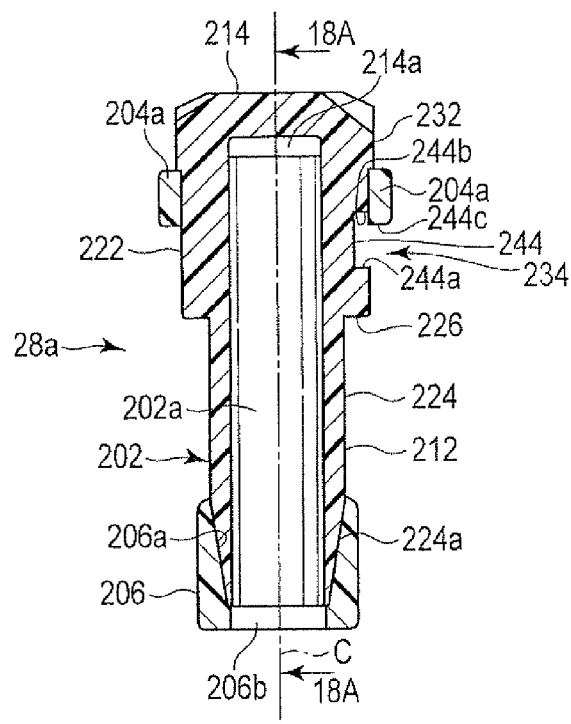
FIG. 18B is a cross-sectional view taken along a line 18B-18B in FIG. 18A, showing a state that the nozzle is attached to the distal end hard portion of the insertion portion of the endoscope according to the first modification of the second embodiment.
Figure 19A:
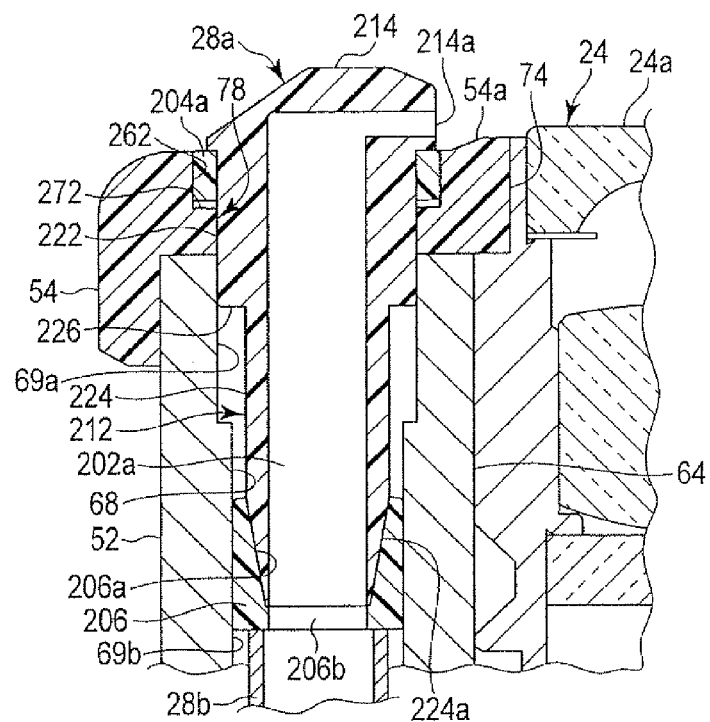
FIG. 19A is a schematic longitudinal cross-sectional view taken along a line 16A-16A in FIG. 15, showing a state that the nozzle is attached to the distal end hard portion of the insertion portion of the endoscope according to the first modification of the second embodiment.
Figure 19B:
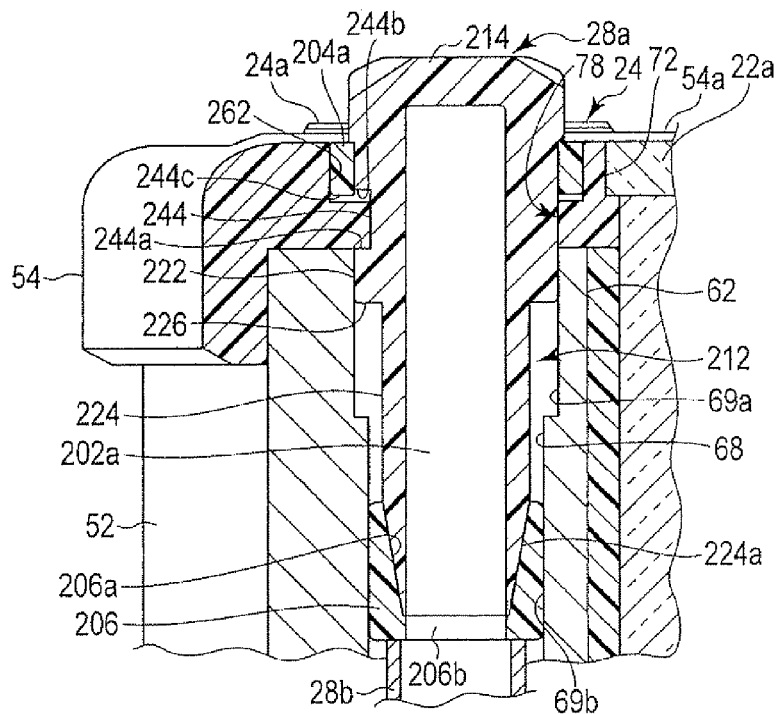
FIG. 19B is a schematic longitudinal cross-sectional view taken along a line 16B-16B in FIG. 15, showing a state that the nozzle is attached to the distal end hard portion of the insertion portion of the endoscope according to the first modification of the second embodiment.

As shown in FIG. 18A and FIG. 18B, the annular portion 204a is formed by extending the annular portion 204 shown in FIG. 11A and FIG. 11B toward the coupling portion 206 side so that it can protrude downward from the upper end surface 244b of the large-diameter portion 222. That is, the end surface 244c of the annular portion 204a provided on the side where it is isolated from the flange portion 232 is used as an upper end portion of the circumferential groove 244.

It is to be noted that, a protruding length of the end surface 244c of the annular portion 204a protruding downward from the upper end surface 244b of the large-diameter portion 222 can be appropriately set based on a height from the accommodating portion 252 to the lower end surface 244a, a thickness of the protruding portion 274, elastic force (self-restoration properties) of the annular portion 204a or the coupling portion 206, and others.

A function of the endoscope 10 according to this modification will now be briefly explained. Here, a description will be given as to a case that the air supply/water supply nozzle 28a is attached to the distal end hard portion 42 of the insertion portion 12 in the endoscope 10.

The proximal end of the coupling portion 206 of the nozzle 28a is mounted on the distal end of the air supply/water supply pipe 28b on the inner side of the small-diameter portion 69b of the air supply/water supply hole portion 68. The end surface 244c of the annular portion 204a of the nozzle 28a provided on the side where it is isolated from the flange portion 232 is mounted on the surfaces of the mounting portion 272 and the protruding portion 274 in the hole portion 78 of the distal end cover 54.

In this state, when the cylindrical body 212 is pushed into the hole portion 78 of the distal end cover 54 and the hole portion 68 of the distal end portion main body 52, the end surface 244c of the annular portion 204a is pressed against the surfaces of the mounting portion 272 and the protruding portion 274 in the hole portion 78 of the distal end cover 54 by the elastic force of the annular portion 204a. Moreover, the protruding portion 274 is arranged in the circumferential groove 244 against the pressing force of the end surface 244c of the annular portion 204a. In this state, the cylindrical body 212 is revolved about the central axis C of the hole portion 78 of the distal end cover 54 and the hole portion 68 of the distal end portion main body 52, and the end portion 276b of the protruding portion 274 is relatively moved along the circumferential groove 244 toward the regulating surface 256a of the second axial groove 246. At this time, slide movement is carried out while pressing the front surface of the protruding portion 274 with the end surface 244c of the annular portion 204a and pressing the back surface of the protruding portion 274 with the lower end surface 244a. That is, the protruding portion 274 is relatively moved toward the second axial groove 246 while holding the front surface and the back surface of the protruding portion 274.

The elastically deformed annular portion 204a exercises recovery force to recover the state that it presses the surface of the protruding portion 274 to its original state. Therefore, pressing force of the elastically deformed annular portion 204a enables the protruding portion 274 of the hole portion 78 of the distal end cover 54 to be accommodated in the accommodating portion 252 through the second axial groove 246 of the nozzle 28a.

At this time, it is preferable that a gap between the upper end surface 244c and the lower end surface 244a of the annular portion 204a is smaller than a thickness of the protruding portion 274, and the protruding portion 274 can slide between the upper end surface 244c and the lower end surface 244a of the annular portion 204a in a state that the pressing force is applied to the upper end surface 244c of the annular portion 204a by using the surface of the protruding portion 274. That is, when a height between the bottom surface of the accommodating portion 252 and the lower end surface 244a is smaller than the thickness of the protruding portion 274, exercising the pressing force to accommodate the protruding portion 274 in the accommodating portion 252 with use of the upper end surface 244c of the annular portion 204a is preferable.

It is to be noted that the coupling portion 206 elastically deforms and exercises the restoring force as described in the second embodiment.

Using the annular portion 204a enables maintaining the state that the nozzle 28a is engaged with the distal end hard portion 42 with the elastic force of the coupling portion 206 as well as the elastic force of the annular portion 204a. Therefore, as compared with the case explained in the second embodiment, the force applied from the air supply/water supply pipe 28b to the coupling portion 206 at the time of attachment/detachment of the nozzle 28a can be set small. That is, the maximum force applied from the air supply/water supply pipe 28b to the coupling portion 206 can be reduced. Moreover, in the state that the distal end hard portion 42 includes the nozzle 28a attached thereto, a distance between the accommodating portion 252 and the upper end surface 244c can be reduced to be smaller than the distance between the accommodating portion 252 and the upper end surface 244b explained in the second embodiment. Therefore, even if the distal end surface 54a of the distal end cover 54 is pressed and the nozzle 28a is pushed in toward the inner side of the distal end hard portion 42, the movement of the protruding portion 274 can be regulated with use of the upper end surface 244c.

In this modification, although the description has been given by using the coupling portion 206 explained in the second embodiment, using the coupling portion 86 explained in the first embodiment is also preferable. In this case, the elastic force of the annular portion 204a enables maintaining the state that the distal end cover 54 includes the nozzle 28a attached thereto.

[Second Modification]

A second modification according to the second embodiment will now be described with reference to FIG. 20 to FIG. 22. In this modification, like reference numerals denote members equal to those explained in the first embodiment including each modification and the second embodiment including the first modification, and a detailed description thereof will be omitted.

As shown in FIG. 20, the groove portion 234 is removed from the large-diameter portion 222 of the nozzle 28a, namely, the first axial groove 242, the circumferential groove 244, and the second axial groove 246 are removed. Further, a protrusion 282 protruding outward in the radial direction is formed on the large-diameter portion 222 in place of the groove portion 234. The protrusion 282 includes a surface 282a parallel to the end surface 244b of the annular portion 204 and a surface 282b orthogonal or substantially orthogonal to the surface 282a, and it is provided at a position away from the annular portion 204. Furthermore, the annular portion 204 and the protrusion 282 of the cylindrical body 212 of the core member 202 form the engagement portion (the second engagement portion) in cooperation with each other.

As shown in FIG. 21A and FIG. 21B, the air supply/water supply hole portion 78 of the distal end cover 54 includes the annular wall 262 and the engagement portion 264.

The engagement portion 264 is provided at the edge portion of the hole portion 78 like the second embodiment. The engagement portion 264 includes a C-shaped mounting portion 292 on which the annular portion 204 is mounted, an axial groove (a concave portion) 294 which is formed as a notch portion of the mounting portion 292 and through which the protrusion 282 passes, and protruding portions 296 and 298 which protrude on the back surface of the distal end cover 54 and engage with the protrusion 282. An opposed circumferential width between the protruding portions 296 and 298 is slightly larger than a circumferential width of the protrusion 282. Moreover, in regard to protruding lengths of the protruding portions 296 and 298 from the back surface of the distal end cover 54, the protruding portion 298 preferably has a larger protruding length. Therefore, the mounting portion 292 and the axial groove 294 form an axial support portion that allows the movement of the core member 202 in a predetermined range along the axial direction in the axial groove 294 with respect to the distal end cover 54, supports the annular portion 204 on the mounting portion 292, and supports the core member 202 with respect to the distal end cover 54. Additionally, the protrusion 282 and the protruding portions 296 and 298 form a locking portion that allows the movement of the core member 202 in a predetermined range along the circumferential direction with respect to the distal end cover 54 and locks the core member 202 with respect to the distal end cover 54.

In case of attaching the nozzle 28a to the distal end hard portion 42, the protrusion 282 of the nozzle 28a is arranged to pass through the axial groove 294 of the distal end cover 54, and the nozzle 28a is revolved about its central axis C, whereby the surfaces 282a and 282b of the protrusion 282 of the nozzle 28a can be engaged with the protruding portions 296 and 298 formed on the back surface of the distal end cover 54. That is, the protrusion 282 of the nozzle 28a can be arranged between the protruding portions 296 and 298. It is to be noted that the coupling portion 206 of the nozzle 28a is engaged with the distal end portion main body 52 as described in the second embodiment.

In case of removing the nozzle 28a from the distal end hard portion 42, the protrusion 282 of the nozzle 28a is allowed to get over a protruding portion 296 formed on the back surface of the distal end cover 54, and it is arranged in the axial groove (the concave portion) 294 of the distal end cover 54. In this state, the nozzle 28a is pulled out of the distal end cover 54.

That is, the large-diameter portion 222 of the nozzle 28a can be detachably engaged with the distal end cover 54, and the coupling portion 206 of the nozzle 28a can be detachably engaged with the distal end portion main body 52.

Therefore, even when the nozzle 28a and the distal end cover 54 having the structures like the second modification of the second embodiment are provided, these members can be used like the second embodiment.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope comprising:
a cylindrical distal end portion main body which is provided at a distal end portion of an insertion portion and which includes a first hole portion; and
a distal end cover which is attached to the distal end portion main body and which includes a second hole portion coaxially provided with the first hole portion and a first engagement portion provided at an edge portion of the second hole portion; and
a nozzle which is arranged to pass through the first hole portion of the distal end portion main body and the second hole portion of the distal end cover, wherein
the nozzle includes:
a cylindrical core member which includes:
one end, the other end, a flow path through which the fluid is allowed to flow from the other end toward the one end, and
a cover member which includes:
a nozzle opening configured to eject a fluid, and arranged at the one end of the core member and arranged at a position protruding from a distal end surface of the distal end cover;
a second engagement portion which is provided on an outer side of the core member, which is elastically deformable, has self-restoration properties, and is configured to engage the first engagement portion such that the second engagement portion (i) is fixedly positioned with the first engagement portion in an appressed state, and (ii) secures water-tightness; and
a cylindrical coupling portion which is arranged at the other end of the core member and which is coupled with the first hole portion of the distal end portion main body and is configured to secure water-tightness,
the first engagement portion of the distal end cover includes one of an annular protruding portion which is configured to press the second engagement portion toward the inside of the core member, and an annular concave groove,
the second engagement portion further includes an annular convex portion engaged with the annular concave groove when the first engagement portion of the distal end cover includes the annular concave groove, and
the nozzle is detachably coupled with the distal end portion main body and the distal end cover such that the nozzle is removable and either (i) reattachable, or (ii) replaceable by an alternate nozzle, wherein the alternate nozzle includes (a) an alternate nozzle opening similar to the nozzle opening, (b) an alternate second engagement portion similar to the second engagement portion, and (c) an alternate cylindrical coupling portion similar to the cylindrical coupling portion, and wherein the convex portion of the second engagement portion of the nozzle is disengaged from the concave groove of the distal end cover, the coupling portion of the nozzle is disengaged from the first hole portion of the distal end portion main body, and the nozzle is removed from the distal end portion main body and the distal end cover, thereafter, an alternate convex portion of the alternate second engagement portion of the alternate nozzle is engaged with the concave groove of the distal end cover, the alternate second engagement portion of the alternate nozzle is configured to engage the first engagement portion and secure water-tightness, and the alternate coupling portion of the alternate nozzle is coupled with the first hole portion and is configured to secure water-tightness.

2. The endoscope according to claim 1, wherein the second engagement portion of the nozzle includes an annular concave groove which is pressed by the protruding portion when the first engagement portion of the distal end cover includes the protruding portion.

3. The endoscope according to claim 1, wherein
the distal end portion main body includes a through hole communicating with the first hole portion, and
the core member includes on an outer peripheral surface thereof a boss portion engaged with the through hole.

4. The endoscope according to claim 1, wherein
the core member includes an annular concave portion on an outer peripheral surface thereof,
the coupling portion is arranged on the annular concave portion, and
one end of the coupling portion is away from a step of the annular concave portion.

5. The endoscope according to claim 1, wherein the core member includes on an outer peripheral surface thereof an annular flange which abuts on a distal end surface of the distal end main body.

6. The endoscope according to claim 1, wherein
each of the first engagement portion and the second engagement portion includes:
an axial support portion which supports the core member at a predetermined position with respect to the distal end cover and allows movement of the core member in a predetermined range along the axial direction with respect to the distal end cover;
a circumferential movement allowing portion which allows movement of the core member in a predetermined range along the circumferential direction with respect to the distal end cover; and
a locking portion which is configured to lock the core member at a predetermined position with respect to the distal end cover.

7. The endoscope according to claim 1, wherein the coupling portion is elastically deformable, has self-restoration properties to hold its shape, and is formed in such a manner that a proximal end side of the coupling portion is appressed against the first hole portion when the nozzle is attached to the distal end portion main body.

8. The endoscope according to claim 1, wherein at least one of the cover member, the core member, and the coupling portion includes a movement regulating portion which is configured to regulate movement of the nozzle with respect to the distal end portion main body.

9. The endoscope according to claim 8, wherein at least one of the cover member, the core member, and the coupling portion includes an axial movement regulating portion which is configured to regulate movement of the nozzle in the axial direction with respect to the distal end portion main body.

10. The endoscope according to claim 8, wherein at least one of the cover member, the core member, and the coupling portion includes a circumferential movement regulating portion which is configured to regulate movement of the nozzle in the circumferential direction with respect to the distal end portion main body.

11. The endoscope according to claim 1, wherein
the cover member and the coupling portion are made of a resin material, and
the core member is configured to fix the cover member and the coupling portion and made of a metal material which is less deformable than the cover member and the coupling portion.

12. The endoscope according to claim 1, wherein the core member is made of a harder material than the coupling portion.

13. An endoscope comprising:
a cylindrical distal end portion main body which is provided at a distal end portion of an insertion portion and which includes a first hole portion; and
a distal end cover which is attached to the distal end portion main body and which includes a second hole portion coaxially provided with the first hole portion and a first engagement portion provided at an edge portion of the second hole portion; and
a nozzle which is arranged to pass through the first hole portion of the distal end portion main body and the second hole portion of the distal end cover, wherein
the nozzle includes:
a cylindrical core member which includes:
one end, the other end, a flow path through which the fluid is allowed to flow from the other end toward the one end, and
a cover member which includes:
a nozzle opening configured to eject a fluid, and arranged at the one end of the core member and arranged at a position protruding from a distal end surface of the distal end cover;
a second engagement portion which is provided on an outer side of the core member, which is elastically deformable, has self-restoration properties, and is configured to secure water-tightness when the second engagement portion is engaged with the first engagement portion in an appressed state; and
a cylindrical coupling portion which is arranged at the other end of the core member and which is coupled with the first hole portion of the distal end portion main body,
the first engagement portion of the distal end cover includes one of an annular protruding portion which is configured to press the second engagement portion toward the inside of the core member, and an annular concave groove,
the second engagement portion further includes an annular convex portion engaged with the annular concave groove when the first engagement portion of the distal end cover includes the annular concave groove,
the nozzle is detachably fixed to the distal end portion main body and the distal end cover such that the nozzle is reusable upon reattachment, the second engagement portion includes:
an annular portion which has self-recovery properties and which is arranged on an outer periphery of the core member; and
a groove portion which is formed at a position where a first axial groove, a circumferential groove formed to be continuous with the first axial groove, and a second axial groove formed to be continuous with the circumferential groove are adjacent to the annular portion,
the first engagement portion includes a protruding portion which is configured to pass through the first axial groove, the circumferential groove, and the second axial groove in the mentioned order when the nozzle is disposed to the distal end portion main body, and is configured to pass through the second axial groove, the circumferential groove, and the first axial groove in the mentioned order when the nozzle is removed from the distal end portion main body, and
the second axial groove includes an accommodating portion, which is configured to accommodate the protruding portion when the nozzle is disposed to the distal end portion main body, at a position facing the annular portion.

14. An endoscope comprising:
a cylindrical distal end portion main body which is provided at a distal end portion of an insertion portion and which includes a first hole portion; and
a distal end cover which is attached to the distal end portion main body and which includes a second hole portion coaxially provided with the first hole portion and a first engagement portion provided at an edge portion of the second hole portion; and
a nozzle which is arranged to pass through the first hole portion of the distal end portion main body and the second hole portion of the distal end cover, wherein
the nozzle includes:
a cylindrical core member which includes:
one end, the other end, a flow path through which the fluid is allowed to flow from the other end toward the one end, and
a cover member which includes:
a nozzle opening configured to eject a fluid, and arranged at the one end of the core member and arranged at a position protruding from a distal end surface of the distal end cover;
a second engagement portion which is provided on an outer side of the core member, which is elastically deformable, has self-restoration properties, and is configured to secure water-tightness when the second engagement portion is engaged with the first engagement portion in an appressed state; and
a cylindrical coupling portion which is arranged at the other end of the core member and which is coupled with the first hole portion of the distal end portion main body,
the first engagement portion of the distal end cover includes one of an annular protruding portion which is configured to press the second engagement portion toward the inside of the core member, and an annular concave groove,
the second engagement portion further includes an annular convex portion engaged with the annular concave groove when the first engagement portion of the distal end cover includes the annular concave groove, the nozzle is detachably fixed to the distal end portion main body and the distal end cover such that the nozzle is reusable upon reattachment, the second engagement portion has self-restoration properties and includes an annular portion arranged on the outer periphery of the core member and a protrusion provided on the outer side of the core member, and the first engagement portion includes:
- an axial groove through which the protrusion is configured to pass through the distal end surface of the distal end cover and a back surface of the distal end cover in the mentioned order when the nozzle is disposed to the distal end portion main body and the protrusion is configured to pass through the back surface of the distal end cover and the distal end surface of the distal end cover in the mentioned order when the nozzle is from the distal end portion main body; and
- a projection portion which is arranged on the back surface of the distal end cover and engaged with the protrusion.

\* \* \* \* \*